(12) United States Patent
Jarrett et al.

(10) Patent No.: US 10,226,417 B2
(45) Date of Patent: Mar. 12, 2019

(54) DRUG DELIVERY SYSTEMS AND APPLICATIONS

(76) Inventors: Peter Jarrett, Lexington, MA (US); Rami El-Hayek, Norwood, MA (US); Amarpreet S. Sawhney, Lexington, MA (US); Sarah Guedez, Melrose, MA (US)

( * ) Notice: Subject to any disclaimer, the term of this patent is extended or adjusted under 35 U.S.C. 154(b) by 227 days.

(21) Appl. No.: 13/234,428

(22) Filed: Sep. 16, 2011

(65) Prior Publication Data
US 2013/0071462 A1  Mar. 21, 2013

(51) Int. Cl.
| A61K 9/14 | (2006.01) |
| A61K 9/00 | (2006.01) |
| A61K 9/06 | (2006.01) |
| A61K 9/50 | (2006.01) |
| A61K 38/00 | (2006.01) |

(52) U.S. Cl.
CPC ............. *A61K 9/0024* (2013.01); *A61K 9/06* (2013.01); *A61K 9/5015* (2013.01); *A61K 38/00* (2013.01)

(58) Field of Classification Search
CPC ........ A61K 9/141; A61K 9/143; A61K 9/145; A61K 9/146; A61K 9/16; A61K 9/1617; A61K 9/1623; A61K 9/1629; A61K 9/1652
USPC ........................................ 424/486, 487, 501
See application file for complete search history.

(56) References Cited

U.S. PATENT DOCUMENTS

| | | |
|---|---|---|
| 3,640,714 A | 2/1972 | Etes |
| 3,779,942 A | 12/1973 | Bolles |
| 3,949,073 A | 4/1976 | Daniels et al. |
| 3,981,303 A | 9/1976 | Higuchi et al. |
| 3,991,766 A | 11/1976 | Schmitt et al. |
| 4,014,335 A | 3/1977 | Arnold |
| 4,101,380 A | 7/1978 | Rubinstein et al. |
| 4,107,288 A | 8/1978 | Oppenheim et al. |
| 4,207,893 A | 6/1980 | Michaels |
| 4,268,495 A | 5/1981 | Muxfeldt et al. |
| 4,414,976 A | 11/1983 | Schwarz et al. |
| 4,456,711 A | 6/1984 | Pietsch et al. |
| 4,472,542 A | 9/1984 | Nambu |
| 4,507,466 A | 3/1985 | Tomalia et al. |
| 4,530,840 A | 7/1985 | Tice et al. |
| 4,568,737 A | 2/1986 | Tomalia et al. |
| 4,631,188 A | 12/1986 | Stoy et al. |
| 4,646,730 A | 3/1987 | Schonfeld et al. |
| 4,664,857 A | 5/1987 | Nambu |
| 4,693,887 A | 9/1987 | Shah |
| 4,717,378 A | 1/1988 | Perrault et al. |
| 4,734,097 A | 3/1988 | Tanabe et al. |
| 4,740,534 A | 4/1988 | Matsuda et al. |
| 4,741,872 A | 5/1988 | DeLuca et al. |
| 4,760,131 A | 7/1988 | Sundsmo et al. |
| 4,803,075 A | 2/1989 | Wallace et al. |
| 4,826,945 A | 5/1989 | Cohn et al. |
| 4,828,857 A | 5/1989 | Sharma et al. |
| 4,837,381 A | 6/1989 | Steber et al. |
| 4,839,345 A | 6/1989 | Doi et al. |
| 4,911,926 A | 3/1990 | Henry et al. |
| 4,925,677 A | 5/1990 | Feijen |
| 4,938,763 A | 7/1990 | Dunn et al. |
| 4,952,581 A | 8/1990 | Bito et al. |
| 4,979,959 A | 12/1990 | Guire |
| 5,024,742 A | 6/1991 | Nesburn et al. |
| 5,041,292 A | 8/1991 | Feijen |
| 5,093,319 A | 3/1992 | Higham et al. |
| 5,100,992 A | 5/1992 | Cohn et al. |
| 5,122,614 A | 6/1992 | Zalipsky |
| 5,143,662 A | 9/1992 | Chesterfield et al. |
| 5,147,647 A | 9/1992 | Darougar et al. |
| 5,152,782 A | 10/1992 | Kowligi et al. |
| 5,158,152 A | 10/1992 | Nemoto et al. |
| 5,160,745 A | 11/1992 | DeLuca et al. |
| 5,162,430 A | 11/1992 | Rhee et al. |
| 5,192,743 A | 3/1993 | Hsu et al. |
| 5,198,220 A | 3/1993 | Damani |
| 5,213,580 A | 5/1993 | Slepian et al. |
| 5,227,372 A | 7/1993 | Folkman |
| 5,232,984 A | 8/1993 | Hubbell et al. |
| 5,266,325 A | 11/1993 | Kuzma et al. |
| 5,278,202 A | 1/1994 | Dunn et al. |
| 5,283,063 A | 2/1994 | Freeman |
| 5,296,228 A | 3/1994 | Chang et al. |
| 5,296,504 A | 3/1994 | Stjernchantz et al. |
| 5,304,595 A | 4/1994 | Rhee et al. |
| 5,306,500 A | 4/1994 | Rhee et al. |

(Continued)

FOREIGN PATENT DOCUMENTS

| EP | 0443743 B1 | 5/1991 |
| EP | 0732109 A1 | 9/1996 |

(Continued)

OTHER PUBLICATIONS

US 6,214,374, 04/2001, Schmirler et al. (withdrawn)
Ibuprofen Drug Facts Data Sheet.*
Capric Acid Data Sheet.*
Ibuprofren Drug Bank entry.*
Capric Acid Drug Bank entry.*
Muheem et al; A review on strategies for oral delivery of proteins and peptides and their clinical perspectives, King Saud University, Saudi Pharmaceutical Journal, 2014.*
PubChem Lauric Acid entry (http://pubchem.ncbi.nlm.nih.gov/compound/3893).*
PubChem: Lauric Acid (http://pubchem.ncbi.nlm.nih.gov/compound/3893).*

(Continued)

*Primary Examiner* — Micah Paul Young
(74) *Attorney, Agent, or Firm* — Christensen, Fonder, Dardi & Herbert PLLC; Curtis Herbert

(57) ABSTRACT

Certain embodiments of the invention include medical materials and methods comprising a biodegradable hydrophilic hydrogel comprising dispersed lipophilic particles that comprise a therapeutic agent, wherein the lipophilic particles have a low water solubility in physiological saline at physiological temperature.

40 Claims, 4 Drawing Sheets

(56) References Cited

U.S. PATENT DOCUMENTS

| | | |
|---|---|---|
| 5,322,691 A | 6/1994 | Darougar et al. |
| 5,324,775 A | 6/1994 | Rhee et al. |
| 5,328,955 A | 7/1994 | Rhee et al. |
| 5,330,768 A | 7/1994 | Park et al. |
| 5,334,137 A | 8/1994 | Freeman |
| 5,368,563 A | 11/1994 | Lonneman et al. |
| 5,376,375 A | 12/1994 | Rhee et al. |
| 5,380,536 A | 1/1995 | Hubbell et al. |
| 5,385,561 A | 1/1995 | Cerny |
| 5,395,618 A | 3/1995 | Darougar et al. |
| 5,409,703 A | 4/1995 | McAnalley et al. |
| 5,410,016 A | 4/1995 | Hubbell et al. |
| 5,413,791 A | 5/1995 | Rhee et al. |
| 5,416,587 A | 5/1995 | Riccobono et al. |
| 5,426,148 A | 6/1995 | Tucker |
| 5,431,639 A | 6/1995 | Shaw |
| 5,446,090 A | 8/1995 | Harris |
| 5,446,091 A | 8/1995 | Rhee et al. |
| 5,455,027 A | 10/1995 | Zalipsky et al. |
| 5,462,990 A | 10/1995 | Hubbell et al. |
| 5,470,911 A | 11/1995 | Rhee et al. |
| 5,475,052 A | 12/1995 | Rhee et al. |
| 5,480,914 A | 1/1996 | Meadows |
| 5,482,927 A | 1/1996 | Maniar et al. |
| 5,510,418 A | 4/1996 | Rhee et al. |
| 5,514,379 A | 5/1996 | Weissleder et al. |
| 5,514,380 A | 5/1996 | Song et al. |
| 5,527,856 A | 6/1996 | Rhee et al. |
| 5,529,914 A | 6/1996 | Hubbell et al. |
| 5,530,528 A | 6/1996 | Houki et al. |
| 5,543,441 A | 8/1996 | Rhee et al. |
| 5,550,187 A | 8/1996 | Rhee et al. |
| 5,550,188 A | 8/1996 | Rhee et al. |
| 5,565,215 A | 10/1996 | Gref et al. |
| 5,565,519 A | 10/1996 | Rhee et al. |
| 5,567,435 A | 10/1996 | Hubbell et al. |
| 5,567,440 A | 10/1996 | Hubbell et al. |
| 5,573,934 A | 11/1996 | Hubbell et al. |
| 5,578,638 A | 11/1996 | Brazzell et al. |
| 5,583,114 A | 12/1996 | Barrows et al. |
| 5,587,175 A | 12/1996 | Viegas et al. |
| 5,589,194 A | 12/1996 | Tsuei et al. |
| 5,612,050 A | 3/1997 | Rowe et al. |
| 5,612,052 A | 3/1997 | Shalaby |
| 5,618,563 A | 4/1997 | Berde et al. |
| 5,624,840 A | 4/1997 | Naughton et al. |
| 5,626,863 A | 5/1997 | Hubbell et al. |
| 5,627,233 A | 5/1997 | Hubbell et al. |
| 5,631,329 A | 5/1997 | Yin et al. |
| 5,643,464 A | 7/1997 | Rhee et al. |
| 5,650,173 A | 7/1997 | Ramstack et al. |
| 5,662,712 A | 9/1997 | Pathak et al. |
| 5,665,840 A | 9/1997 | Pohlmann et al. |
| 5,681,576 A | 10/1997 | Henry |
| 5,702,716 A | 12/1997 | Dunn et al. |
| 5,705,194 A | 1/1998 | Wong et al. |
| 5,707,643 A | 1/1998 | Ogura et al. |
| 5,714,159 A | 2/1998 | Shalaby |
| 5,718,916 A | 2/1998 | Scherr |
| 5,723,269 A | 3/1998 | Akagi et al. |
| 5,731,005 A | 3/1998 | Ottoboni et al. |
| 5,733,950 A | 3/1998 | Dunn et al. |
| 5,741,292 A | 4/1998 | Mendius |
| 5,741,323 A | 4/1998 | Pathak et al. |
| 5,744,545 A | 4/1998 | Rhee et al. |
| 5,752,974 A | 5/1998 | Rhee et al. |
| 5,770,229 A | 6/1998 | Tahihar et al. |
| 5,773,019 A | 6/1998 | Ashton et al. |
| 5,773,025 A | 6/1998 | Baichwal |
| 5,776,445 A | 7/1998 | Cohen et al. |
| 5,776,493 A | 7/1998 | Barclay et al. |
| 5,786,421 A | 7/1998 | Rhee et al. |
| 5,800,373 A | 9/1998 | Hubbell et al. |
| 5,800,541 A | 9/1998 | Rhee et al. |
| 5,800,841 A | 9/1998 | Rhee et al. |
| 5,801,033 A | 9/1998 | Hubbell et al. |
| 5,807,581 A | 9/1998 | Rosenblatt et al. |
| 5,814,621 A | 9/1998 | Kanaya et al. |
| 5,820,882 A | 10/1998 | Hubbell et al. |
| 5,823,198 A | 10/1998 | Jones et al. |
| 5,824,037 A | 10/1998 | Fogarty et al. |
| 5,830,171 A | 11/1998 | Wallace |
| 5,834,274 A | 11/1998 | Hubbell et al. |
| 5,837,226 A | 11/1998 | Jungherr et al. |
| 5,843,743 A | 12/1998 | Hubbell et al. |
| 5,844,016 A | 12/1998 | Sawhney et al. |
| 5,844,023 A | 12/1998 | Tomka |
| 5,849,035 A | 12/1998 | Pathak et al. |
| 5,849,839 A | 12/1998 | Hubbell et al. |
| 5,851,508 A | 12/1998 | Greff et al. |
| 5,858,746 A | 1/1999 | Hubbell et al. |
| 5,869,096 A | 2/1999 | Barclay et al. |
| 5,874,500 A | 2/1999 | Rhee et al. |
| 5,879,688 A | 3/1999 | Coury et al. |
| 5,888,493 A | 3/1999 | Sawaya |
| 5,900,245 A | 5/1999 | Sawhney et al. |
| 5,932,462 A | 8/1999 | Harris et al. |
| 5,936,035 A | 8/1999 | Rhee et al. |
| 5,962,023 A | 10/1999 | Jamiolkowski et al. |
| 5,972,375 A | 10/1999 | Truter et al. |
| 5,973,014 A | 10/1999 | Funk et al. |
| 5,981,607 A | 11/1999 | Ding et al. |
| 5,986,043 A | 11/1999 | Hubbell et al. |
| 6,017,301 A | 1/2000 | Schwartz et al. |
| 6,046,305 A | 4/2000 | Choi |
| 6,051,248 A | 4/2000 | Sawhney et al. |
| 6,051,648 A | 4/2000 | Rhee et al. |
| 6,060,582 A | 5/2000 | Hubbell et al. |
| 6,071,875 A | 6/2000 | Clark et al. |
| 6,082,362 A | 7/2000 | Webb |
| 6,083,524 A | 7/2000 | Sawhney et al. |
| 6,110,484 A | 8/2000 | Sierra |
| 6,121,341 A | 9/2000 | Sawhney et al. |
| 6,123,667 A | 9/2000 | Poff et al. |
| 6,129,761 A | 10/2000 | Hubbell et al. |
| 6,132,986 A | 10/2000 | Pathak et al. |
| 6,149,614 A | 11/2000 | Dunshee et al. |
| 6,149,931 A | 11/2000 | Schwartz et al. |
| 6,152,943 A | 11/2000 | Sawhney |
| 6,153,211 A | 11/2000 | Hubbell et al. |
| 6,154,671 A | 11/2000 | Parel et al. |
| 6,156,345 A | 12/2000 | Chudzik et al. |
| 6,156,531 A | 12/2000 | Pathak et al. |
| 6,162,241 A | 12/2000 | Coury et al. |
| 6,165,201 A | 12/2000 | Sawhney et al. |
| 6,165,489 A | 12/2000 | Berg et al. |
| 6,166,130 A | 12/2000 | Rhee et al. |
| 6,171,600 B1 | 1/2001 | Dahms |
| 6,176,871 B1 | 1/2001 | Pathak et al. |
| 6,177,095 B1 | 1/2001 | Sawhney et al. |
| 6,177,514 B1 | 1/2001 | Pathak et al. |
| 6,179,862 B1 | 1/2001 | Sawhney |
| 6,180,141 B1 * | 1/2001 | Lemercier ............ A61K 9/1617 424/479 |
| 6,187,330 B1 | 2/2001 | Wang et al. |
| 6,201,065 B1 | 3/2001 | Pathak et al. |
| 6,214,966 B1 | 4/2001 | Harris |
| 6,217,896 B1 | 4/2001 | Benjamin |
| 6,220,246 B1 | 4/2001 | Chandler et al. |
| 6,231,892 B1 | 5/2001 | Hubbell et al. |
| 6,251,382 B1 | 6/2001 | Greenwald et al. |
| 6,258,351 B1 | 7/2001 | Harris |
| 6,258,870 B1 | 7/2001 | Hubbell et al. |
| 6,261,544 B1 | 7/2001 | Coury et al. |
| 6,277,394 B1 | 8/2001 | Sierra |
| 6,287,588 B1 | 9/2001 | Shih et al. |
| 6,290,729 B1 | 9/2001 | Slepian et al. |
| 6,296,603 B1 | 10/2001 | Turnlund et al. |
| 6,297,240 B1 | 10/2001 | Embleton |
| 6,303,102 B1 | 10/2001 | Schlichte |
| 6,306,922 B1 | 10/2001 | Hubbell et al. |
| 6,312,725 B1 | 11/2001 | Wallace et al. |
| 6,316,441 B1 | 11/2001 | Dean et al. |
| 6,319,240 B1 | 11/2001 | Beck |

(56) References Cited

U.S. PATENT DOCUMENTS

| | | | |
|---|---|---|---|
| 6,322,593 B1 | 11/2001 | Pathak et al. | |
| 6,323,278 B2 | 11/2001 | Rhee et al. | |
| 6,331,184 B1 | 12/2001 | Abrams | |
| 6,331,313 B1 | 12/2001 | Wong et al. | |
| 6,335,335 B2 | 1/2002 | Higashiyama et al. | |
| 6,352,682 B2 | 3/2002 | Leavitt et al. | |
| 6,371,975 B2 | 4/2002 | Cruise et al. | |
| 6,379,373 B1 | 4/2002 | Sawhney | |
| 6,387,977 B1 | 5/2002 | Sawhney et al. | |
| 6,410,645 B1 | 6/2002 | Pathak et al. | |
| 6,458,147 B1 | 10/2002 | Cruise et al. | |
| 6,458,889 B1 | 10/2002 | Trollsas et al. | |
| 6,465,001 B1 | 10/2002 | Hubbell et al. | |
| 6,475,508 B1 | 11/2002 | Schwartz et al. | |
| 6,479,079 B1 | 11/2002 | Pathak et al. | |
| 6,495,127 B1 | 12/2002 | Wallace et al. | |
| 6,503,731 B2 | 1/2003 | Marx et al. | |
| 6,514,534 B1 | 2/2003 | Sawhney | |
| 6,517,824 B1 | 2/2003 | Kohn et al. | |
| 6,528,107 B2 | 3/2003 | Chinn et al. | |
| 6,534,591 B2 | 3/2003 | Rhee et al. | |
| 6,566,406 B1 | 5/2003 | Pathak et al. | |
| 6,569,463 B2 | 5/2003 | Patel et al. | |
| 6,579,519 B2 | 6/2003 | Maitra et al. | |
| 6,589,549 B2 | 7/2003 | Shih et al. | |
| 6,596,471 B2 | 7/2003 | Pathak et al. | |
| 6,602,975 B2 | 8/2003 | Hubbell et al. | |
| 6,605,294 B2 | 8/2003 | Sawhney | |
| 6,610,033 B1 | 8/2003 | Melanson et al. | |
| 6,624,245 B2 | 9/2003 | Wallace et al. | |
| 6,632,446 B1 | 10/2003 | Hubbell et al. | |
| 6,632,457 B1* | 10/2003 | Sawhney | A61K 9/1647 424/486 |
| 6,639,014 B2 | 10/2003 | Pathak et al. | |
| 6,673,093 B1 | 1/2004 | Sawhney | |
| 6,679,605 B2 | 1/2004 | Zhou et al. | |
| 6,689,148 B2 | 2/2004 | Sawhney et al. | |
| 6,692,759 B1 | 2/2004 | Wong et al. | |
| 6,699,493 B2 | 3/2004 | Wong | |
| 6,703,047 B2 | 3/2004 | Sawhney et al. | |
| 6,709,668 B2 | 3/2004 | Won et al. | |
| 6,710,126 B1 | 3/2004 | Hirt et al. | |
| 6,719,750 B2 | 4/2004 | Varner et al. | |
| 6,747,090 B2 | 6/2004 | DeGroot et al. | |
| 6,818,018 B1 | 11/2004 | Sawhney | |
| 6,833,408 B2 | 12/2004 | Sehl et al. | |
| 6,858,229 B1* | 2/2005 | Hubbell | A61K 9/0019 424/422 |
| 6,883,408 B2 | 4/2005 | Shinga | |
| 6,887,974 B2 | 5/2005 | Pathak | |
| 6,902,743 B1 | 6/2005 | Setterstrom et al. | |
| 6,911,227 B2 | 6/2005 | Hubbell et al. | |
| 6,911,496 B2 | 6/2005 | Rhee et al. | |
| 6,916,857 B2 | 7/2005 | Won et al. | |
| 6,923,986 B2 | 8/2005 | Pathak et al. | |
| 6,923,988 B2 | 8/2005 | Patel et al. | |
| 6,936,005 B2 | 8/2005 | Poff et al. | |
| 6,958,212 B1 | 10/2005 | Hubbell et al. | |
| 6,962,979 B1 | 11/2005 | Rhee | |
| 7,009,034 B2 | 3/2006 | Pathak et al. | |
| 7,017,580 B2 | 3/2006 | Prescott et al. | |
| 7,025,990 B2 | 4/2006 | Sawhney | |
| 7,057,019 B2 | 6/2006 | Pathak | |
| 7,060,297 B2 | 6/2006 | Karakelle et al. | |
| 7,129,210 B2 | 10/2006 | Lowinger et al. | |
| 7,141,248 B2 | 11/2006 | Hodd et al. | |
| 7,153,519 B2 | 12/2006 | Hubbell et al. | |
| 7,211,651 B2 | 5/2007 | Pathak | |
| 7,220,270 B2 | 5/2007 | Sawhney et al. | |
| RE39,713 E | 7/2007 | Sawhney et al. | |
| 7,238,364 B2 | 7/2007 | Sawhney et al. | |
| 7,247,314 B2 | 7/2007 | Hnojewyj et al. | |
| 7,273,896 B2 | 9/2007 | Daniloff et al. | |
| 7,332,566 B2 | 2/2008 | Pathak et al. | |
| 7,413,752 B2 | 8/2008 | Sawhney | |
| 7,589,057 B2 | 9/2009 | Chang et al. | |
| 7,648,713 B2 | 1/2010 | Sawhney | |
| 7,862,538 B2 | 1/2011 | Sawhney et al. | |
| 2002/0026176 A1 | 2/2002 | Varner et al. | |
| 2002/0064513 A1 | 5/2002 | Maitra et al. | |
| 2002/0071869 A1 | 6/2002 | Bures et al. | |
| 2002/0071874 A1 | 6/2002 | Olejnik et al. | |
| 2002/0114778 A1 | 8/2002 | Xia et al. | |
| 2002/0138154 A1* | 9/2002 | Li et al. | 623/66.1 |
| 2002/0192280 A1* | 12/2002 | Hunter | A61K 9/0014 424/465 |
| 2002/0197300 A1 | 12/2002 | Schultz et al. | |
| 2003/0012734 A1 | 1/2003 | Pathak et al. | |
| 2003/0017199 A1 | 1/2003 | Woodward et al. | |
| 2003/0064105 A1* | 4/2003 | Kim | A61K 9/1617 424/493 |
| 2003/0143280 A1 | 7/2003 | El-Sherif et al. | |
| 2003/0147849 A1 | 8/2003 | Warne et al. | |
| 2003/0175324 A1 | 9/2003 | Robinson et al. | |
| 2003/0185892 A1 | 10/2003 | Bell et al. | |
| 2003/0191426 A1 | 10/2003 | Lerner et al. | |
| 2004/0009205 A1 | 1/2004 | Sawhney | |
| 2004/0037889 A1 | 2/2004 | Richeal et al. | |
| 2004/0076602 A1 | 4/2004 | Harris | |
| 2004/0086479 A1 | 5/2004 | Grinstaff et al. | |
| 2004/0098096 A1 | 5/2004 | Eton | |
| 2004/0131582 A1 | 7/2004 | Grinstaff et al. | |
| 2004/0228862 A1 | 11/2004 | Shelton et al. | |
| 2005/0043220 A1 | 2/2005 | Guyer et al. | |
| 2005/0158392 A1 | 7/2005 | Kim et al. | |
| 2005/0169882 A1 | 8/2005 | Lowe et al. | |
| 2005/0197614 A1 | 9/2005 | Pritchard et al. | |
| 2005/0208095 A1 | 9/2005 | Hunter et al. | |
| 2005/0232972 A1 | 10/2005 | Odrich | |
| 2005/0238692 A1 | 10/2005 | Hughes | |
| 2005/0244464 A1 | 11/2005 | Hughes | |
| 2005/0244467 A1 | 11/2005 | Nivaggioli et al. | |
| 2005/0255144 A1 | 11/2005 | Schultz | |
| 2005/0271727 A1 | 12/2005 | Yao | |
| 2005/0277864 A1 | 12/2005 | Haffner et al. | |
| 2006/0002963 A1 | 1/2006 | Rabinovich-Guilatt et al. | |
| 2006/0013859 A1 | 1/2006 | Yamada et al. | |
| 2006/0024350 A1 | 2/2006 | Varner et al. | |
| 2006/0039979 A1 | 2/2006 | Yamada et al. | |
| 2006/0057222 A1 | 3/2006 | Linhardt et al. | |
| 2006/0074370 A1 | 4/2006 | Zhou | |
| 2006/0079599 A1 | 4/2006 | Arthur | |
| 2006/0100288 A1 | 5/2006 | Bague et al. | |
| 2006/0147409 A1 | 7/2006 | Pathak et al. | |
| 2006/0177481 A1 | 8/2006 | Sawhney | |
| 2006/0182771 A1 | 8/2006 | Dor et al. | |
| 2006/0182781 A1 | 8/2006 | Hughes et al. | |
| 2006/0182783 A1 | 8/2006 | Hughes et al. | |
| 2006/0193899 A1 | 8/2006 | Sawhney | |
| 2006/0258698 A1 | 11/2006 | Mudumba et al. | |
| 2006/0286173 A1 | 12/2006 | Yamada et al. | |
| 2007/0160647 A1 | 7/2007 | Pritchard et al. | |
| 2007/0185033 A1 | 8/2007 | Gefter et al. | |
| 2007/0196497 A1 | 8/2007 | Pouliquen et al. | |
| 2007/0197776 A1 | 8/2007 | Pathak | |
| 2007/0202186 A1 | 8/2007 | Yamamoto et al. | |
| 2007/0224246 A1 | 9/2007 | Hughes et al. | |
| 2007/0231366 A1 | 10/2007 | Sawhney et al. | |
| 2007/0233240 A1 | 10/2007 | Frank et al. | |
| 2007/0243230 A1 | 10/2007 | De Juan, Jr. et al. | |
| 2007/0248567 A1 | 10/2007 | Pathak et al. | |
| 2007/0270345 A1 | 11/2007 | Gardner et al. | |
| 2007/0275027 A1 | 11/2007 | Wen et al. | |
| 2008/0014144 A1 | 1/2008 | Saltzman et al. | |
| 2008/0038316 A1 | 2/2008 | Wong et al. | |
| 2008/0038317 A1 | 2/2008 | Chang et al. | |
| 2008/0045911 A1 | 2/2008 | Borgia et al. | |
| 2008/0114092 A1 | 5/2008 | Sawhney | |
| 2008/0124376 A1 | 5/2008 | Pruitt et al. | |
| 2008/0124389 A1 | 5/2008 | Jenkins et al. | |
| 2008/0124400 A1 | 5/2008 | Liggins et al. | |
| 2008/0132444 A1 | 6/2008 | Li et al. | |
| 2008/0171091 A1 | 7/2008 | Wood et al. | |
| 2008/0187568 A1 | 8/2008 | Sawhney | |

(56) References Cited

U.S. PATENT DOCUMENTS

| | | | |
|---|---|---|---|
| 2008/0220047 | A1 | 9/2008 | Sawhney et al. |
| 2008/0233173 | A1 | 9/2008 | Whitcup et al. |
| 2008/0241223 | A1 | 10/2008 | Nivaggioli et al. |
| 2008/0254086 | A1* | 10/2008 | Brown ............... A61K 9/0024 424/422 |
| 2008/0268020 | A1 | 10/2008 | Philips et al. |
| 2008/0279944 | A1 | 11/2008 | Sawhney |
| 2009/0017097 | A1 | 1/2009 | Sawhney et al. |
| 2009/0104248 | A1 | 4/2009 | Rapacki et al. |
| 2009/0105749 | A1 | 4/2009 | De Juan et al. |
| 2009/0118702 | A1 | 5/2009 | Lazar |
| 2009/0215923 | A1 | 8/2009 | Carnahan et al. |
| 2009/0227981 | A1 | 9/2009 | Bennett |
| 2009/0240276 | A1 | 9/2009 | Ainpour et al. |
| 2009/0252781 | A1 | 10/2009 | Sawhney et al. |
| 2009/0264861 | A1 | 10/2009 | Jain et al. |
| 2010/0036488 | A1 | 2/2010 | De Juan, Jr. et al. |
| 2010/0104654 | A1 | 4/2010 | Robinson et al. |
| 2010/0158980 | A1 | 6/2010 | Kopczynski et al. |
| 2010/0209478 | A1 | 8/2010 | Sawhney et al. |
| 2011/0142936 | A1 | 6/2011 | Campbell et al. |
| 2012/0071865 | A1 | 3/2012 | Jarrett et al. |

FOREIGN PATENT DOCUMENTS

| | | | |
|---|---|---|---|
| EP | 1704878 | A2 | 9/2006 |
| WO | 9705185 | A2 | 2/1997 |
| WO | 9722371 | A1 | 6/1997 |
| WO | 9835631 | A1 | 3/1998 |
| WO | 2006031358 | A2 | 3/2006 |
| WO | 2006031388 | A2 | 3/2006 |
| WO | 2007001926 | A2 | 1/2007 |
| WO | 2007005249 | A2 | 1/2007 |
| WO | 2008035376 | A2 | 3/2008 |
| WO | WO 2009105614 | A2 * | 8/2009 ............. A61L 27/46 |

OTHER PUBLICATIONS

International Search Report and Written Opinion from corresponding PCT Application No. PCT/US2012/053026, 15 pages, dated Jan. 29, 2013.
Atha et al. "Mechanism of Precipitation of Proteins by Polyethylene Glycols" The Journal of Biological Chemistry, Dec. 10, 1981, pp. 12108-12117, vol. 256 No. 23, USA.
Bailey et al. "Synthesis of Polymerized Vesicles with Hydrolyzable Linkages" Macromolecules, 1992, pp. 3-11, vol. 25 No. 1, University of Maryland College Park, Maryland.
Bos et al. "Controlled Release of Pharmaceutical Proteins from Hydrogels" Business Briefing: Pharmatech, 2002, pp. 1-5.
Campbell et al. "Evaluation of Absorbable Surgical Sealants: In Vitro Testing", pp. 1-4, Confluent Surgical, Inc., Waltham, MA.
"Confluent Surgical DuraSeal Packaging", Ref. 10-505, LCN-2005-101, 2 Pages.
"CoSeal Surgical Sealant", 0700169 Rev. 2, Mar. 2006, 2 Pages.
Dong et al. "Dextran Permeation Through Poly (N-Isopropylacrylamide) Hydrogels", J. Biomater. Sci. Polymer Edn, 1994, pp. 473-484, vol. 5 No. 5.
Dunn et al. "Evaluation of the SprayGel™ adhesion barrier in the rat cecum abrasion and rabbit uterine horn adhesion models", Fertility and Sterility, Feb. 2001, pp. 411-416, vol. 75 No. 2, Elsevier Science Inc.
Dunn et al. "Rat(abdominal) & Rabbit (Pelvic) Studies", Confluent Surgical Inc Preclinical Studies, 2000, 2 pages.
Galeska et al. "Controlled Release of Dexamethasone from PLGA Microspheres Embedded Within Polyacid-Containing PVA Hydrogels", The AAPS Journal, Sep. 2, 2005, pp. E231-E240 vol. 7.
Gander et al., "Crosslinked Poly(Alkylene Oxides) for the Preparation of Controlled Release Micromatrices", Journal of Controlled Release, 1988, pp. 271-283, vol. 5, Elsevier Science Publishers B.V., Amsterdam.
Gayet et al. "High water content BSA-PEG hydrogel for controlled release device: Evaluation of the drug release properties", Journal of Controlled Release, 1996, pp. 177-184, vol. 38, Elsevier Science B.V.
Geerling et al. "Plugs for Occlusion of the Lacrimal Drainage System", Surgery for the Dry Eye, 2008, pp. 193-212, vol. 41, Würzburg, Germany.
Hermann "Lipidic Implants for Pharmaceutical Proteins: Mechanisms of Release and Development of Extruded Devices", Dissertation Ludwig-Maximilians-University, 2007, pp. 1-220, München.
Hill-West et al. "Prevention of Postoperative Adhesions in the Rat by In Situ Photopolymerization of Bioresorbable Hydrogel Barriers" Obstetrics & Gynecology, Jan. 1994, pp. 59-64, vol. 83 No. 1.
Hoare et al. "Hydrogels in drug delivery: Progress and challenges", ScienceDirect, Jan. 19, 2008, pp. 1993-2007, Elsevier Ltd.
Hyon "Biodegradable Poly (Lactic Acid) Microspheres for Drug Delivery Systems", Yonsei Medical Journal, 2000, pp. 720-734, vol. 41 No. 6.
Jarrett et al. "Bioabsorbable Hydrogel Tissue Barrier: In Situ Gelation Kinetics" Society for Biomaterials 21st Annual Meeting, Mar. 1995, 2 pages.
Kimura et al. "Injectable Microspheres with Controlled Drug Release for Glaucoma Filtering Surgery" Investigative Ophthalmology & Visual Science, Nov. 1992, pp. 3436-3441, vol. 33 No. 12.
Kissel et al. "Parenteral depot-systems on the basis of biodegradable polyesters", Journal of Controlled Release, 1991, pp. 27-42, vol. 16, Elsevier Science Publishers.
Kissel et al. "ABA-triblock copolymers from biodegradable polyester A-blocks and hydrophilic poly(ethylene oxide) B-blocks as a candidate for in situ forming hydrogel delivery systems for proteins" Advanced Drug Delivery Reviews, 2002, pp. 99-134, vol. 54, Elsevier Science B.V.
Klibanov et al. "Activity of amphipathic poly( ethylene glycol) 5000 to prolong the circulation time of liposomes depends on the liposome size and is unfavorable for immunoliposome binding to target" Biochimica et Biophysica Acta, 1991, pp. 142-148, vol. 1062, Elsevier Science Publishers.
Lasic et al. "Sterically stabilized liposomes: a hypothesis on the molecular origin of the extended circulation times" Biochimica et Biophysica Acta, 1991, pp. 187-192, vol. 1070, Elsevier Science Publishers.
Lou et al. "Drug release characteristics of phase separation pHEMA sponge materials" ScienceDirect, 2004, pp. 5071-5080, Elsevier Ltd.
Mathiowitz et al. "Polyanhydride Microspheres as Drug Carriers I. Hot-Melt Microencapsulation" Journal of Controlled Release, 1987, pp. 13-22, vol. 5, Elsevier Science Publishers, Amsterdam.
Mayhew et al. "Characterization of Lipsomes Prepared Using a Microemulsifier" Biochimica et Biophysica Acta, 1984, pp. 169-174, vol. 775, Elsevier.
Mettler et al. "Prospective Clinical Trial of SprayGel as a Barrier to Adhesion Formation an Interim Analysis", The Journal of the American Association of Gynecologic Laparoscopists, Aug. 2003, pp. 339-344, vol. 10 No. 3.
Nihant et al. "Polyactide Microparticles Prepared by Double Emulsjon— Evaporation" Journal of Colloid and Interface Science, 1995, pp. 55-65, vol. 173, Academic Press, Inc.
Park et al. "Biodegradable Hydrogels for Drug Delivery" Technomic Publishing Co. Inc., Purdue University, School of Pharmacy.
Park "Enzyme-digestible swelling hydrogels as platforms for long-term oral drug delivery: synthesis and characterization" Biomaterials, Sep. 1988, pp. 435-442, vol. 9, Butterworth & Co. Ltd.
Reddy et al. "Polyurethane Microspheres as Drug Carriers" Macromolecular Report, 1995, pp. 789-799, Marcel Dekker, Inc.
Sawhney et al. Bioerodible Hydrogels Based on Photopolymerized Poly(ethylene glycol)-co-poly(a-hydroxy acid) Diacrylate Macromers, Macromolecules, Oct. 16, 1992, pp. 581-587, vol. 26, American Chemical Society.
Sawhney et al. "Optimization of photopolymerized bioerodible hydrogel properties for adhesion prevention" Journal of Biomedical Materials Research, 1994, pp. 831-838, vol. 28, John Wiley & Sons, Inc.
Sawhney et al. "Rabbit (Pericardial) Adhesion Study", Confluent Surgical Inc. Preclinical Studies, 2 Pages.
Srividya et al. "Sustained ophthalmic delivery of ofloxacin from a pH triggered in situ gelling system" Journal of Controlled Release, Feb. 21, 2001, pp. 205-211, vol. 73, Elsevier Science.

(56) References Cited

OTHER PUBLICATIONS

Tabata et al. "Controlled Delivery Systems for Proteins Using Polyanhydride Microspheres" Pharmaceutical Research, 1993, pp. 487-496, vol. 10 No. 4, Plenum Publishing Corporation.
Torchilin et al. "Liposome-Polymer Systems Introduction of Liposomes Into a Polymer Gel and Ppeparation of the Polymer Gel Inside a Liposome" Polymer Science U.S.S.R., May 20, 1987, pp. 2307-2312, vol. 30 No. 10, Pergamon Press plc., Poland.
Zalipsky et al. "Esterification of Polyethylene Glycols" J. Macromol. Sci.-Chem., 1984, pp. 839-845, vol. A21, Department of Organic Chemistry the Hebrew University of Jerusalem, Israel.
Zustiak et al. "Characterization of Protein Release From Hydrolytically Degradable Poly(Ethylene Glycol) Hydrogels" Biotechnology and Bioengineering, Aug. 5, 2010, pp. 197-206, vol. 108 No. 1, Wiley Perodicals, Inc.
Yasukawa et al., "Biodegradable Scleral Plugs for Vitreoretinal Drug Delivery", Advanced Drug Delivery Review, vol. 52:25-36 (2001).

* cited by examiner

DRUG DELIVERY SYSTEMS AND APPLICATIONS

TECHNICAL FIELD

The technical field relates to drug delivery systems and applications, and includes delivery of drugs using particles entrapped in a hydrogel matrix.

BACKGROUND

Drug delivery is a field of research focused on administrating a pharmaceutical compound to achieve a therapeutic effect in a patient. The biological target, such as a receptor or cell, must be exposed to the drug for a length of time and at a concentration that is adequate to achieve the therapeutic effect. The drug must be administered to the patient, with the common routes of administration being oral, topical, transmucosal, and inhalation routes. There are many different approaches to achieving a controlled release of a drug over time so that the drug may be delivered effectively and conveniently.

SUMMARY

An embodiment of the system involves a hydrophilic hydrogel comprising dispersed lipophilic particles that contain a water soluble therapeutic agent. The particles may be made with molecules that are lipophilic but nonetheless have a low water solubility, meaning a water solubility in the range of about 0.001 to about 0.5 mg/ml at 20° C. The particles may be made so they are solid at 20° C. and/or have a melting point of between about 25° C. and about 60° C. Moreover, the particles, in some embodiments, may be made with low water soluble lipophilic materials that have a molecular weight of no more than about 2000. Hydrophobic and/or hydrophilic therapeutic agents may be used.

An embodiment of the invention is a process of making a medical material comprising coating a peptide powder with a low water soluble lipophilic compound to make particles and dispersing the particles in a medical hydrogel implant. The particles may be made so they are solid at 20° C. and/or have a melting point of between about 25° C. and about 60° C. The materials for making the particles, not including the therapeutic agent, may be chosen, in some embodiments, to have a molecular weight of no more than about 2000. One process for making the material is that the lipophilic compound is provided as a melt, and wherein coating a peptide powder with a lipophilic compound to make particles comprises mixing the powder with the melt to coat the powder with the compound, cooling the mixture to a solid, and breaking up the solid to form the particles. An embodiment is the process wherein coating a peptide powder with a lipophilic compound to make particles comprises mixing the peptide powder with a lipophilic compound to form a mixture of the powder and the compound, dispersing the mixture into a solution to form droplets of the mixture, and cooling the droplets to a solid phase and thereby form the particles. The peptide may be a protein having a secondary and/or a tertiary structure. The protein may be processed and released so that the protein is not denatured.

An embodiment is a method of delivering a therapeutic agent to a patient comprising placing a hydrogel in a patient that comprises a particle that comprises a low water soluble lipophilic compound and a therapeutic agent, with the agent being released into the patient. The hydrogel may be premolded and then implanted, or made in situ. The implant may be substantially dehydrated upon implantation. The material may be placed into the patient at or near an eye at a location, e.g., chosen from the group consisting of intravitreal, cornea, subconjunctival, juxta-scleral, and punctal. The material may be placed into the patient, e.g., in a tissue or organ, including subcutaneous, intramuscular, in a potential space of a body, or in a natural cavity or opening.

An embodiment is a method of delivering a therapeutic agent to a patient comprising placing a hydrogel in a patient that comprises a particle that comprises a low water soluble lipophilic compound and a therapeutic agent, with the agent being released into the patient.

An embodiment is a kit comprising an applicator, a hydrogel precursor, and lipophilic particles that comprise a therapeutic agent, wherein the lipophilic particles are solid at 20° C. and have a low water solubility in physiological saline at physiological temperature, with the applicator being adapted to deliver a mixture of the particles and the precursor to an eye. The lipophilic particles may comprise, e.g., at least one member chosen from the group consisting of lauric acid, capric acid, methyl stearate, and methyl palmitate. Lipophilic particles may also be made from biodegradable polymers, that display the characteristics of biocompatibility and melting behavior so as to allow microparticle fabrication and protein or peptide encapsulation by a melt type process.

DETAILED DESCRIPTION

Systems for well-controlled and long-term controlled release of a therapeutic agent are described herein. An embodiment of the system involves a biodegradable hydrophilic hydrogel comprising dispersed lipophilic particles that contain a water soluble therapeutic agent. The particles may be made with molecules that have a low water solubility, meaning a water solubility of less than about 0.1 mg/ml at 20° C. It has been observed that such particles degrade or dissolve rapidly and rapidly discharge their therapeutic agent contents in vivo, but the same particles degrade or dissolve slowly and discharge their contents slowly when they are inside the hydrogel in vivo.

Figure 1A:
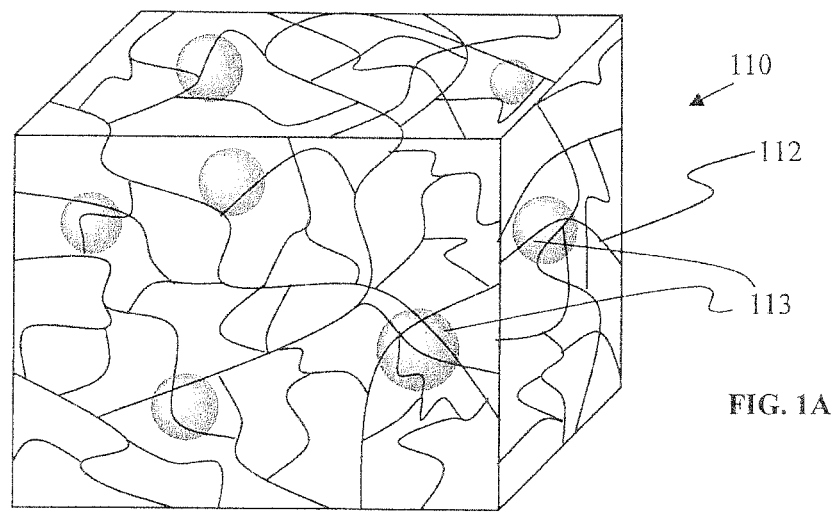
FIG. 1A is an illustration of a hydrogel network containing dispersed lipophilic particles.
Figure 1B:
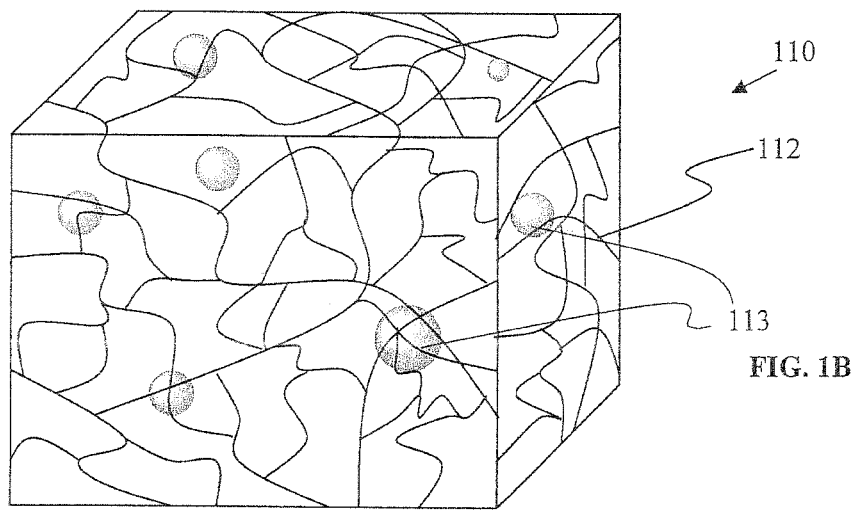
FIG. 1B is an illustration of the network of FIG. 1A at a later time point.
Figure 1C:
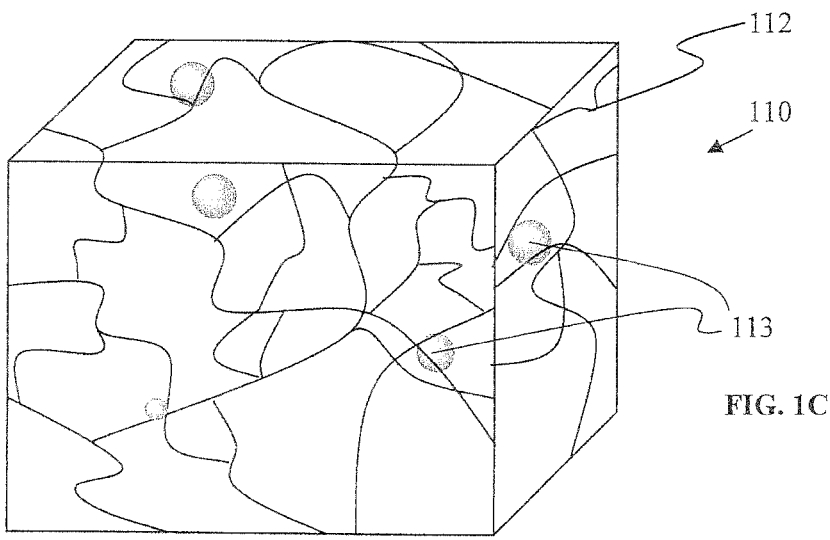
FIG. 1C is an illustration of the network of FIG. 1B at a later time point.

FIG. 1 depicts a volume of hydrogel 110 comprising interconnected polymeric network 112 and particles 113. At the time of formation, in FIG. 1A, the particles are entrapped within the network. The particles slowly degrade or dissolve, releasing entrapped therapeutic agents. Without being bound to a particular theory, the low water solubility material of the particles distributes in the network, and establishes a dynamic quasi-equilibrium with the network and the particles, with the lipophilic material slowly moving out of the network into a sink, such as a body of a patient. As the particles degrade or dissolve, in FIG. 1B, they remain entrapped in the network. In FIG. 1C, the network's degradation appreciably contributes to shifting the quasi-equilibrium in favor of dissipation of the lipophilic material into the sink, allowing the material to move out of the matrix more quickly. The network eventually dissipates altogether. Lipophilicity is useful but, if water solubility is also provided, then the material may undergo bioresorption in vivo. Too much water solubility, however, causes difficulty processing particles in aqueous based depots, and may alter the local pH or ionic strength in a way unfavorable to the stability of the therapeutic agent. FIG. 1 is one embodiment of the system that exemplifies how the system's kinetics can impact the release process. Other embodiments are described below.

These systems are in contrast to some conventional controlled release approaches that rely on erosion of a hydrogel or a particle to deliver an agent. These systems are also in contrast to approaches that rely on diffusion of an agent through a hydrogel or through a particle as a rate limiting step to control release of the agent into the patient.

An aspect of the systems that is disclosed herein relates to a large increase in control release time caused by combining the hydrogels and the lipophilic particles. Examples 1-3 detail processes used to form particles from low water soluble lipophilic materials containing albumin. The protein albumin was used to model a water soluble therapeutic agent protein. The particles were combined with hydrogel precursors that were mixed to form a hydrogel, Example 4. In Example 5, the particles, when placed by themselves into a sink (a very large volume relative to the sample) of physiological saline, released their loaded agents in about a day. In contrast, the same particles in the hydrogels released only a fraction of the total amount of the agent in the same time. Further testing has shown that the proteins can be fully recovered (Example 6). These and other aspects of the inventive embodiments described herein were unexpected, surprising, and not predictable.

Particles and Processes of Formation

One process for making particles involves creation of a lipophilic material as a solid that contains a therapeutic agent, and breaking-up the material to make the particles. The material may be, e.g., ground in a ball mill or with a mortar and pestle, or chopped or diced with knives or wires. Or the material could be cut-up in a blender. Another process involves forcing the material through a mesh, collecting the fragments, and passing them through the same mesh or another mesh until a desired size is reached. Another process may entail shearing the coarsely ground particles into a finer particle size using homogenizers.

One embodiment involves preparing a therapeutic agent and blending the agent with a low-water soluble lipophilic material to make a solid that is then broken up. The agent is mixed with a liquid melt of the lipophilic material, blended together, and allowed to cool to room temperature. The term melt refers to an essentially pure liquid, i.e., a liquid without solvent. Instead of a melt, a solvent may be present with the lipophilic material. The solvent may be removed by subsequent processing, e.g., evaporation. The temperature of the mixture may be controlled so that it is greater than the melting point of the lipophilic material and less than a predetermined value in the range of about 45 to about 90° C.; artisans will immediately appreciate that all the ranges and values within the explicitly stated ranges are contemplated, e.g., less than about 50° C. or less than about 60° C.

Lipophilic is a term that means a material that is soluble in hydrophobic medium. Lipophilic materials tend to be insoluble in water. Lipophilic particles are described herein, however, that are water soluble. The particles may be made with lipophilic molecules that have a low water solubility. A low-water soluble lipophilic material has a solubility in 20° C. distilled water in the range of about 0.001 to about 0.5 mg/ml. Artisans will immediately appreciate that materials falling within the ranges and values within the explicitly stated ranges are contemplated, e.g., between about 0.01 mg/ml to about 0.07 or between about 0.003 and about 0.09 mg/ml, or from 0.001 to about 0.2 mg/ml. Table 1 provides examples of such materials, along with other materials for comparison. Low-water soluble lipophilic materials include, for example, capric acid, lauric acid, methyl stearate, and methyl palmitate. Low-water soluble fatty acids are generally useful, recognizing that many fatty acids are not low-water soluble, and that the form of the fatty acid affects solubility, e.g., with a free carboxylic acid terminus generally being more soluble than a salted form, or a triglyceride. Many fatty acids are not low-water soluble fatty acids. Amphiphiles, e.g., common phospholipids, are generally not soluble in water and, instead of dissolving, form micelles or other structures based on a phase-separation. A single lipophilic material may be used, or a blend of one or more materials may be used to make a particle. Embodiments include particles that consist essentially of at least one agent and at least one low-water soluble lipophilic material (or molecule or polymer), with essentially meaning that all other materials that are present are at least as soluble in water as the lipophilic material, do not denature proteins, and are present in an amount of less than about 10% by weight.

TABLE 1

| Systemic name | Trivial name | Molecular wt. | Melting point (° C.) | Solubility in water at 20° C. (mg/ml) | Methyl ester solubility (mg/ml) |
|---|---|---|---|---|---|
| butanoic | butyric | 88.1 | −7.9 | infinite | |
| pentanoic | valeric | | | — | |
| hexanoic | caproic | 116.1 | −3.4 | 9.7 | |
| octanoic | caprylic | 144.2 | 16.7 | 0.7 | |
| nonanoic | pelargonic | 158.2 | 12.5 | — | |
| decanoic | capric | 172.3 | 31.6 | 0.15 | 0.062 |
| dodecanoic | lauric | 200.3 | 44.2 | 0.055 | 0.0048 |
| tetradecanoic | myristic | 228.4 | 53.9 | 0.02 | |
| hexadecanoic | palmitic | 256.4 | 63.1 | 0.007 | 0.00001 |
| heptadecanoic | margaric (daturic) | 270.4 | 61.3 | — | |
| octadecanoic | stearic | 284.4 | 69.6 | 0.003 | 0.0000012 |

The low water soluble lipophilic materials, or other lipophilic materials, may be chosen to have a molecular weight of no more than about 2000 (atomic mass less than or equal to about 2000 Daltons); artisans will immediately appreciate that all the ranges and values within the explicitly stated ranges are contemplated, e.g., from about 200 to about 500, from about 100 to about 1000 or less than about 350. An advantage of this molecular weight range is that the low molecular weight provides a sharp transition in melting points; in contrast, a higher molecular weight material will, in general, have a lengthier transition. For example, polylactides or polygalactides conventionally used in the medical arts are a solid below their melting point and are observed to pass from solid to soft to gelatinous to gummy to liquid as they are heated, with the transition taking place over a range of several degrees and an extended time. The low molecular weight materials, however, will transition from solid to liquid over a short time and temperature. Accordingly, embodiments include particles made with a low water soluble lipophilic material with a molecular weight of less than about 2000, or plurality of such materials, that exhibit a predetermined melting point of between about 25° C. and about 60° C.

Lipophilic materials such as low-melting point (about 20° C. to about 60° C., and including ranges in between) fatty acids or other low-melting point lipophilic molecules can be useful for making particles so that materials other than low water soluble materials may be used. Insoluble lipophilic materials as well as lipophilic materials that are more soluble that the low-soluble materials can be used in some circumstances. Accordingly, this disclosure is made with reference to low water soluble lipophilic materials but other lipophilic materials may be similarly made.

The therapeutic agent may be a protein. Proteins are easily denatured. As described herein, however, proteins may be delivered substantially without denaturation. The term substantially without denaturation refers to a protein processed into a particle without modification of the protein's chemical structure (without addition of chemical groups or changes of the existing chemical groups) and without changes to the protein's conformation, i.e., secondary and/or tertiary and/or quaternary structure. The term substantially, in this context, means that no significant differences (p-value <0.05) between processed proteins and control proteins are observed for an averaged test group when tested under routine conditions, e.g., as in the Examples herein. A primary protein structure refers to the amino acid sequence. To be able to perform their biological function, proteins fold into one or more specific spatial conformations, driven by a number of non-covalent interactions such as hydrogen bonding, ionic interactions, Van Der Waals forces, and hydrophobic packing. The term secondary structure refers to the local protein structure, such as local folding. The tertiary structure refers to a particular three-dimensional conformation, including folding. A protein that has secondary and/or tertiary structure thus exhibits local and general structural organization. In contrast, a linear peptide that has no particular conformation does not have secondary and/or tertiary structure. The term native means as found in nature in vivo, so that proteins may be processed into particles and released in a native conformation.

Proteins may be tested for denaturation by a variety of techniques, including enzyme-linked immunosorbent assay (ELISA), isoelectric focusing (IEF), size exclusion chromatography (SEC), high-pressure liquid chromatography (HPLC), circular dichroism (CD), and Fourier Transform Infrared Spectroscopy (FTIR). These tests report parameters such as changes in molecular weight, change in end groups, changes in bonds, changes in hydrophobicity or volume exclusion, and revelation/hiding of antigenic sites. In general, a test by IEF and ELISA may be designed that is adequate to show native conformation after processing, although other tests and test combinations may alternatively be used.

Experimentation has shown that a number of factors can be controlled that contribute to processing and delivery of a protein without denaturation. The protein may be prepared as a powder, with the powder size being chosen in light of the size of the particle. All organic solvents for the proteins may be avoided so that the proteins are only solvated by water and/or water-based physiological solutions (e.g., phosphate buffered solution prepared at physiological pH and osmolarity). Another factor is oxygen, and elimination of oxygen is helpful in processing to avoid denaturation. Another factor is chemical reactions. These may be avoided by processing the protein into an inert material, e.g., blending it with a lipophilic material. As disclosed herein, lipophilic materials may be used to surround the proteins and prevent them from undergoing chemical reactions before they are released in vivo.

One embodiment of particle preparation involves receiving a protein without substantial denaturation, e.g., from a supplier or animal or recombinant source. The protein is lyophilized or concentrated or used as received. The protein is then prepared as a fine powder without denaturation by processing it in a solid state and avoiding high temperatures, moisture, and optionally in an oxygen free environment. Powders may be prepared by, for example, grinding, ball milling, or mortar-and-pestle a solid protein. The powders are then blended with lipophilic materials. The lipophilic materials may be raised to a temperature above their melting point and mixed with the proteins. The mixture is then dispersed into particles (e.g., drops in a cooling bath, gas-cooled spray drying, dispersion or emulsification in aqueous media) or cooled and broken-up. As described above, the temperature for the protein may be limited to a maximum temperature.

Examples 1-3 provide working examples of these processes, and exemplify embodiments of the methods by using lauric acid, methyl stearate, or methyl palmitate. Example 6 details how the proteins are released with a high end-point efficiency, with more than 90% of the total protein being released. Example 7 describes an embodiment of an oxygen-free processing method. Examples 8-10 show that the protein can be released with high end-point efficiency and without changes in structure.

Further embodiments are directed to therapeutic agents that are highly hydrophobic, with a log P of at least about 2; artisans will immediately appreciate that all the ranges and values within the explicitly stated ranges are contemplated, e.g., from about 2 to about +20, from about 2.5 to about 8, or more than 2. The term log P refers to an index for hydrophilicity/hydrophobicity of a compound, the Log P representing the logarithm of the partition coefficient of 1-octanol/water (pH 7.4; buffer solution) obtained by the flask-shaking method, as is well known to artisans. Such embodiments may be prepared, for example, in particles with a molecular weight of less than about 2000 and with a melting point of between about 20 and about 60° C. Moreover, the low water soluble lipophilic compound may also be chosen to have a log P of at least about 2. For instance, the capric acid log P is 3.75, the lauric acid log P is 4.77, the methyl palmitate log P is 7.41 and the methyl stearate log P is 8.43.

The particles may be made by blending, melting, and other approaches that provide for a robust particle without internal covalent and/or ionic crosslinks. Embodiments include particles that comprise at least one agent and at least one low-water soluble lipophilic material and are free of one or more of: crosslinking agents, covalent crosslinks, ionic crosslinks, disulfide bonds, divalent ions, divalent cations, divalent anions, Ba++, Ca++, Mg++, sulfates, sulfites, sulfides, metals, metal ions, copper, and iron.

Moreover, the particles may be made from low water soluble lipophilic materials in a well-controlled manner, and thus may be free of one or more of: amphiphiles, surfactants, triglycerides, phospholipids, phosphate groups, micelles, liposomes, buffering agents, carbonate, bicarbonate, and phosphates. Further, the particles may be free of materials that spontaneously degrade in water by hydrolysis, and thus may be free of one or more of: polylactides, polyglycolides, polycarbonates, polyesters, polyorthoesters, and polyanhydrides. Moreover, the particles may be free of proteins and/or polysaccharides and/or proteoglycans other than the therapeutic agent or agents, and thus may be free of: collagen, albumin, fibrin, fibrinogen, chitin, chitosan, heparan, and hyaluronic acid. The materials may be chosen to be saturated fatty acids, or alternatively unsaturated fatty acids. Triglycerides may be excluded from the particles, or may be chosen to be no more than about 1% to about 10% of the particles; artisans will immediately appreciate that all the ranges and values within the explicitly stated ranges are contemplated, e.g., less than 5%. The particles may be made, for example, by a process that excludes all lipophilic salts and/or glycerol esters of fatty acids, or may be chosen to be no more than about 1% to about 10% of the particles; artisans will immediately appreciate that all the ranges and values within the explicitly stated ranges are contemplated, e.g., less than 5%. Embodiments of the particles may include exclusion of one or more lipophilic salts chosen from the group consisting of: di- or multivalent salts, e.g., calcium or zinc salts; and organic salts (e.g. quaternary ammonium/organics).

The particles may be separated into collections with a desired size range and distribution of sizes by a variety of methods. Very fine control of sizing is available, with sizes ranging from 1 micron to several mm, and with a mean and range of particles sizes being controllable with a narrow distribution. Artisans will immediately appreciate that all the ranges and values within the explicitly stated ranges are contemplated. About 1 to about 500 microns is one such range that is useful, with sizes falling throughout the range and having a mean sizing at one value within the range, and a standard deviation centered around the mean value, e.g., from about 1% to about 100%. A simple method for sizing particles involves using custom-made or standardized sieve mesh sizes. In addition to standard U.S. and Tyler mesh sizes, sieves are also commonly used in the Market Grade, Mill Grade, and Tensile Bolting Cloth. Materials forced through meshes may show deformation so that the particle size is not precisely matched to mesh sizes; nonetheless, mesh sizes may be chosen to achieve a desired a particle size range. A spheroidal particle refers to a particle wherein the longest central axis (a straight line passing through the particle's geometric center) is no more than about twice the length of other central axes, with the particle being a literally spherical or having an irregular shape. A rod-shaped particle refers to a particle with a longitudinal central axis more than about twice the length of the shortest central axis.

Emulsion-based techniques are also available. In one method, particles, e.g., microspheres, are formed from dispersing molten lipophilic material with embedded therapeutic agent in a water/surfactant solution, then cooling to obtain a solidified microparticle dispersion. In another method microparticles are formed from polymerizable hydrophobic macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Additionally, a polymerizable phase, containing all components for reaction, but with a slow polymerization rate, can be introduced into a second immiscible phase where it is dispersed into microspheres prior to polymerization. The polymerization arts also provide for micellar and microemulsion techniques for making particles. The term solid particle refers to a continuous particle, as distinct from a liposome, microcapsule, or micelles that have a hollow portion.

Particles may further be exposed to a stabilizer. Microspheres made with a lipophilic material were observed to crystallize when standing in aqueous solutions in some circumstances. The stabilizer may be, e.g, polyvinyl alcohol (PVA) (see Example 1B), which was found to be an effective stabilizer.

A collection of microparticles may include sets of particles. For instance, some particles may be made to contain a first therapeutic agent, with those particles forming a set within the collection. Other sets are directed to particle sizes, with the sets having distinct shapes or size distributions. As discussed, particles can be made with well-controlled sizes and divided into various sets for combination into a collection.

Other sets are directed to solubility in water. One embodiment involves a plurality of sets each made from different low-water soluble lipophilic materials or different ratios of materials. One application is the use of a plurality of sets with distinct solubilities to promote controlled release of one or more agents. For instance a first agent may be disposed in particles with a first solubility and a second agent disposed in particles with a second solubility. Or the first agent may be disposed in a first collection of particles having a first solubility and also in a second collection of particles having a second solubility. Or a first and a second agent (or more) may be combined together and placed in one or more collections of particles.

Hydrogels and Hydrogel Precursors

Matrices may be prepared and used to encapsulate the particles. Accordingly, embodiments are provided herein for making implantable matrices. Such matrices include matrices with a porosity of more than about 20% v/v; artisans will immediately appreciate that all the ranges and values within the explicitly stated range is contemplated. Hydrogels are an embodiment of such a matrix. Hydrogels are materials that do not dissolve in water and retain a significant fraction (more than 20%) of water within their structure. In fact, water contents in excess of 90% are often known. Hydrogels are often formed by crosslinking water soluble molecules to form networks of essentially infinite molecular weight. Hydrogels with high water contents are typically soft, pliable materials. A hydrogel that has been dried is referred to herein as a dehydrated hydrogel if it will return to a hydrogel state upon exposure to water; this hydrogel would expand in volume if it were exposed to an excess of water and not constrained. The term desiccated refers to a hydrogel essentially having no fluids, bearing in mind that some trace amounts of water may nonetheless be present.

Hydrogels and drug delivery systems as described in U.S. Ser. No. 12/884,466 and U.S. Patent Publication No. 2009/0017097 and 2011/0142936 may be used; which references are hereby incorporated herein by reference for all purposes; in case of conflict, the instant specification is controlling. Low water solubility lipophilic particles comprising a therapeutic agent, e.g., a protein, may be combined with such systems to deliver the agent to a patient.

Hydrogels may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum cross-linked with a polyol such as propylene glycol, and the like, also form hydrogels upon contact with aqueous surroundings.

Synthetic hydrogels may be biostable or biodegradable or biodegradable. Examples of biostable hydrophilic polymeric materials are poly(hydroxyalkyl methacrylate), poly(electrolyte complexes), poly(vinylacetate) cross-linked with hydrolysable or otherwise degradable bonds, and water-swellable lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, with the present specification controlling in case of conflict.

Hydrogels may be made from precursors. The precursors are not hydrogels but are covalently crosslinked with each other to form a hydrogel and are thereby part of the hydrogel. Crosslinks can be formed by covalent or ionic bonds, by hydrophobic association of precursor molecule segments, or by crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein.

Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates.

Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons.

The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two reactive groups can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional, groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. A hydrophilic precursor or precursor portion has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly(oxyalkylenes) or poly(ethylene glycol) or polyethylene glycol are generally hydrophilic.

A precursor may also be a macromolecule (or macromer), which is a molecule having a molecular weight in the range of a thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated: A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

As used herein, the term peptide and polypeptide are used interchangeably in a broad sense to mean a protein, a protein derivative, protein fragment, or sequence of amino acids, including natural or synthetic sequences. The term oligopeptide is a narrow term referring to peptides of less than 30,000 Daltons. Alternatively, natural proteins or polysaccharides may be adapted for use with these methods, e.g., collagens, fibrin(ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivatized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic portion is one that is sufficiently hydrophobic to cause the macromer or copolymer to aggregate to form micelles in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in Patent Application Pub. Nos. US20040086479, US20040131582, WO07005249, WO07001926, WO06031358, or the U.S. counterparts thereof; dendrimers may also be useful as multifunctional precursors, e.g., as in U.S. Pat. Pub. Nos. US20040131582, US20040086479 and PCT Applications No. WO06031388 and WO06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and can not be made by cleaving a naturally occurring protein and can not be made by adding synthetic materials to a protein. Precursors may be non-collagen, non-fibrin, non-fibrinogen), and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. SG refers to succinimidyl glutarate. SS refers to succinimidyl succinate. SAP refers to succinimidyl adipate. SAZ refers to succinimidyl azelate. SS, SG, SAP and SAZ are succinimidyl esters that have an ester group that degrades by hydrolysis in water. Hydrolytically degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. PEG and/or hydrogels, as well as compositions that comprise the same, may be provided in a form that is pharmaceutically acceptable, meaning that it is highly purified and free of contaminants, e.g., pyrogens.

Functional Groups

The precursors have functional groups that react with each other to form the material, either outside a patient, or in situ. The functional groups generally have polymerizable groups for polymerization or react with each other in electrophile-nucleophile reactions or are configured to participate in other polymerization reactions. Various aspects of polymerization reactions are discussed in the precursors section herein.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfosuccinimidyl esters, or as in U.S. Pat. No. 5,410,016, or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfo-succinimidyl esters, N-hydroxysuccinimidyl ester, succin-imidyl ester, epoxide, aldehyde, maleimides, imidoesters and the like. The N-hydroxysuccinimide esters or N-hy-droxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinker reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di- or multifunctional poly (ethylene glycol) can be used.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1,4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2,2-dimethoxy-2-phenyl acetophenone groups, other acetophenone derivatives, thioxanthone groups, benzophenone groups, and camphorquinone groups. Examples of thermally reactive initiators include 4,4' azobis(4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Hydrogels and Swelling

In general, the precursors may be combined to make a covalently-crosslinked hydrogel. The hydrogel may comprise a therapeutic agent, or agents, released over a suitable period of time. Hydrogels may be made beforehand or in situ. When made in situ, the crosslinking reactions generally occur in aqueous solution under physiological conditions. The crosslinking reactions preferably do not release heat of polymerization or require exogenous energy sources for initiation or to trigger polymerization. Formation of hydrogels in situ can result in adherence of the hydrogel to the tissue margins. This adherence will tend to reduce fluid flow into the cavity by the bridging of native molecules across the hydrogel barrier and thereby advantageously reduce seroma formation.

An embodiment is a hydrogel with less swelling. The hydrogel may be generally low-swelling, as measurable by the hydrogel having a weight increasing no more than about 50% upon exposure to a physiological solution in the absence of physical restraints for twenty-four hours relative to a weight of the hydrogel at the time of formation. Swelling may be measured or expressed by weight or volume. Some embodiments swell by weight or by volume no more than about 50%, no more than about 20%, or no more than about 0%; artisans will immediately appreciate that all the ranges and values within the explicitly stated ranges are contemplated, e.g., shrinkage from 10% to 20% (negative swelling), swelling from −10% to no more than 50%. One aspect of swelling is that large changes will increase the difficulty of achieving a desired hydrogel size. For instance, filling a depression in a tissue with a swelling hydrogel will cause the hydrogel to have a height that is not apparent to the user at the time of application and/or gelation. Similarly, swelling (and shrinkage) can create forces that tend to pull the hydrogel away from surrounding tissues so that adherence is affected.

One approach for low-swelling is increase the number of crosslinks or solids content. Increasing in these factors, however, will typically effect the mechanical properties of the gel, with more crosslinks making the gel more brittle but stronger and a higher solids content making the gel stronger. These factors can also increase degradation time and may affect interactions with cells. Another embodiment to reduce swelling is to choose precursors that have a high degree of solvation at the time of crosslinking but subsequently become less solvated and having a radius of solvation that effectively shrinks; in other words, the precursor is spread-out in solution when crosslinked but later contracts. Changes to pH, temperature, solids concentration, and solvent environment can cause such changes; moreover, an increase in the number of branches (with other factors being held effectively constant) will tend to also have this effect. The number of arms are believed to sterically hinder each other so that they spread-out before crosslinking, but these steric effects are offset by other factors after polymerization. In some embodiments, precursors have a plurality of similar charges so as to achieve these effects, e.g., a plurality of functional groups having a negative charge, or a plurality of arms each having a positive charge, or each arm having a functional group of similar charges before crosslinking or other reaction.

Hydrogels described herein can include hydrogels that swell minimally after deposition. Such medical low-swellable hydrogels may have a weight upon polymerization that increases no more than, e.g., about 25%, about 10%, about 5%, about 0% by weight upon exposure to a physiological solution, or that shrink (decrease in weight and volume), e.g., by at least about 5%, at least about 10%, or more. Artisans will immediately appreciate that all ranges and values within or otherwise relating to these explicitly articulated limits are disclosed herein. Unless otherwise indicated, swelling of a hydrogel relates to its change in volume (or weight) between the time of its formation when crosslinking is effectively complete and the time after being placed in in vitro aqueous solution in an unconstrained state for twenty-four hours, at which point it may be reasonably assumed to have achieved its equilibrium swelling state. For most embodiments, crosslinking is effectively complete within no more than about three minutes such that the initial weight can generally be noted at about 15 minutes after formation as Weight at initial formation. Accordingly, this formula is used: % swelling=[(Weight at 24 hours−Weight at initial formation)/Weight at initial formation]*100. The weight of the hydrogel includes the weight of the solution in the hydrogel.

Certain polymerizable hydrogels made using synthetic precursors are known in the medical arts, e.g., as used in products such as FOCALSEAL (Genzyme, Inc.), COSEAL (Angiotech Pharmaceuticals), and DURASEAL (Confluent Surgical, Inc), as in, for example, U.S. Pat. Nos. 6,656,200; 5,874,500; 5,543,441; 5,514,379; 5,410,016; 5,162,430; 5,324,775; 5,752,974; and 5,550,187; each of which are hereby incorporated by reference to the extent they do not contradict what is explicitly disclosed herein. These materials can polymerize too quickly to be injected in a controlled fashion for at least some of the applications described herein. Also, COSEAL and DURASEAL have a high pH, (above pH 9). Another limitation, for some embodiments, for using these materials is that they swell significantly, although a more recently approved DURASEAL EXACT spine sealant is reported to have lower swelling. The swelling of COSEAL and DURASEAL has been measured using an in vitro model in comparison to fibrin sealant (Campbell et al., Evaluation of Absorbable Surgical Sealants: In vitro Testing, 2005). Over a three day test, COSEAL swelled an average of about 558% by weight, DURASEAL increased an average of about 98% by weight, and fibrin sealant swelled about 3%.

Reaction kinetics for these and other matrices and hydrogels generally are controlled in light of the particular functional groups, their concentrations, and the local pH unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction due to their higher concentration of reactive groups, so that some embodiments have at least one precursor with a molecular weight of less than about 1000 or about 2000 Daltons; artisans will immediately appreciate that all the ranges and values within the explicitly stated ranges are contemplated, e.g., from 100 to about 900 Daltons or from 500 to about 1800 Daltons.

The crosslinking density of the resultant biocompatible crosslinked polymer is controlled by the overall molecular weight of the crosslinker and functional polymer and the number of functional groups available per molecule. A lower molecular weight between crosslinks such as 500 will give much higher crosslinking density as compared to a higher molecular weight such as 10,000. The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. Precursors with longer distances between crosslinks are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 3,000 to 100,000; artisans will immediately appreciate that all the ranges and values within the explicitly stated ranges are contemplated e.g., 10,000 to 35,000.

The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%.

Biodegradation

The hydrogel may be made water-degradable, as measurable by the hydrogel losing its mechanical strength and eventually dissipating in vitro in an excess of water by hydrolytic degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, or precursors that degrade into acid or diacids. The term degradation by solvation in water, also referred to as dissolving in water, refers to a process of a matrix gradually going into solution in, which is a process that can not take place for a covalently crosslinked material and materials insoluble in water.

For example, SG (succinimidyl glutarate), SS (succinimidyl succinate), SC (succinimidyl carbonate), SAP (succinimidyl adipate), carboxymethyl hydroxybutyric acid (CM-HBA) may be used and have esteric linkages that are hydrolytically labile. More linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment.

The hydrogel may be water-degradable (hydrolytically degradable), as measurable by the hydrogel being dissolvable in vitro in an excess of water by degradation of water-degradable groups. This test is predictive of hydrolytically-driven dissolution in vivo, a process that is in contrast to cell or protease-driven degradation. The hydrogels can be selected to be absorbable over days, weeks, or months. For instance, different functional groups may be substituted for each other to thereby tune a particular composition's range of degradation, as in Example 11.

A biodegradable linkage in the hydrogel and/or precursor may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

If it is desired that a biocompatible crosslinked matrix be biodegradable or absorbable, one or more precursors having biodegradable linkages present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

Matrix materials may be chosen so that degradation products are absorbed into the circulatory system and essentially cleared from the body via renal filtration. The matrix materials may be hydrogels. One method is to choose precursors that are not broken down in the body, with linkages between the precursors being degraded to return the precursors or precursors with small changes caused by the covalent crosslinking process. This approach is in contrast to choosing biological matrix materials that are destroyed by enzymatic processes and/or materials cleared by macrophages, or that result in by-products that are effectively not water soluble. Materials that are cleared from the body by renal filtration can be labeled and detected in the urine using techniques known to artisans. While there might be at least a theoretical loss of some of these materials to other bodily systems, the normal fate of the material is a kidney clearance process. The term essentially cleared thus refers to materials that are normally cleared through the kidneys.

Visualization Agents

A visualization agent may be used with the hydrogel; it reflects or emits light at a wavelength detectable to a human eye so that a user applying the hydrogel could observe the object when it contains an effective amount of the agent. Agents that require a machine aid for imaging are referred to as imaging agents herein, and examples include: radioopaque contrast agents and ultrasound contrast agents.

Some biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent.

Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. The visualization agent may be present with either reactive precursor species, e.g., a crosslinker or functional polymer solution. The preferred colored substance may or may not become chemically bound to the hydrogel. The visualization agent may be used in small quantities, e.g., 1% weight/volume, more preferably less that 0.01% weight/volume and most preferably less than 0.001% weight/volume concentration; artisans will immediately appreciate that all the ranges and values within the explicitly stated ranges are contemplated.

A visualization agent may also be used with a particle, and may be present with the lipophilic materials used for the same. The agent tends to mark the location of the particle and provides an indication of its presence and dissolution rate.

Drugs or Other Therapeutic Agents for Delivery

Various drugs or other therapeutic agents may be delivered with the systems described herein. The particles made with low water soluble lipophilic materials may be used to deliver a therapeutic agent. The particles may be administered inside a hydrogel. The hydrogel may be preformed or formed in situ. Alternatively, the particles may be administered directly, or in a pharmaceutically acceptable binder or carrier. Other materials may comprise the particles. Water soluble agents are one category of agents that may be delivered. Hydrophobic agents are another category. Small molecule drugs may be delivered, and may be water soluble or hydrophobic.

Proteins are a category of water soluble agents. The particles may be processed so that the proteins are incorporated and released without substantial denaturation and/or in their native conformation. Some anti-vascular endothelial growth factor (VEGF) agents are therapeutic agent proteins. Anti-VEGF therapies are important in the treatment of certain cancers and in age-related macular degeneration. They can involve monoclonal antibodies such as bevacizumab (AVASTIN), antibody derivatives such as ranibizumab (LUCENTIS), or small molecules that inhibit the tyrosine kinases stimulated by VEGF: lapatinib (TYKERB), sunitinib (SUTENT), sorafenib (NEXAVAR), axitinib, and pazopanib. (Some of these therapies target VEGF receptors as opposed to the VEGFs.)

Some conventional ocular drug delivery systems deliver drugs with topical eye drops. For example, after cataract and vitreoretinal surgery, antibiotics are administered dropwise every few hours for several days. In addition, other drugs such as non-steroidal anti inflammatory drugs (NSAIDS) may also need to be given frequently. Some of these eye drops, for example RESTASIS (Allergan), also have a stinging and burning sensation associated with their administration. RESTASIS is indicated for dry eye and has to be used by the patient several times a day. Similarly treatments for other ophthalmic diseases such as cystoid macular edema, diabetic macular edema (DME), and diabetic retinopathy also need administration of steroidal or NSAID drugs. Several vascular proliferative diseases such as macular degeneration are treated using intravitreal injections of VEGF inhibitors. These include drugs such as LUCENTIS and AVASTIN (Genentech) and MACUGEN (OSI). Such drugs may be delivered using the hydrogel-and-particle systems described herein, with the steps of repeated dosings being avoided; e.g., not making new applications of the drug daily, weekly, or monthly, or not using topical eye drops to administer the drug.

Various drug delivery systems are known. These various other systems generally include intravitreal implant reservoir type systems, biodegradable depot systems, or implants that need to be removed (non-erodeable). The state of the art in this regard has been delineated in texts such as "Intraocular Drug Delivery" (Jaffe et al., Taylor & Francis pub., 2006. However, most of these implants either need to be removed at term, can detach from their target site, may cause visual disturbances in the back of the eye or can be inflammatory themselves because of the liberation of a substantial amount of acidic degradation products. These implants are thus made to be very small with a very high drug concentration. Even though they are small, they still need to be deployed with needles over 25 G (25 gauge) in size, or a surgical approach delivery system for implantation or removal as needed. In general, these are localized injections of drug solutions into the vitreous humor or intravitreal implants that use a biodegradable-approach or a removable-reservoir approach. For instance, localized injections delivered into the vitreous humor include anti-VEGF agents LUCENTIS or AVASTIN. POSURDEX (Allergan) is a biodegradable implant with indications for use being diabetic macular edema (DME) or retinal vein occlusions, with a 22 g delivery system used for delivery into the vitreous cavity; these are powerful drugs in a short drug delivery duration setting. The therapeutic agent is in dexamethasone with polylactic/polyglycolic polymer matrix. Trials with POSURDEX for diabetic retinopathy are in progress. And for instance, a Medidure implant (PSIVIDA) is used for DME indications. This implant is about 3 mm in diameter, cylindrical in shape, and non-erodeable. It is placed with a 25 gauge injector delivery system, the therapeutic agent is fluocinolone acetonide, and has a nominal delivery life of 18 months or 36 months (two versions). An intravitreal, removable implant containing triamcinolone acetonide is being tested. Its nominal delivery life is about two years and requires surgical implantation. Its indication is for DME.

In contrast to these conventional systems, these or other therapeutic agents may be delivered using a collection of particles or hydrogels comprising the particles. The particles comprise the agent. The hydrogels can be to be biocompatible for the eye, which is an environment that is distinctly different from other environments. The use of minimally inflammatory materials avoids angiogenesis, which is harmful in the eye in many situations. Biocompatible ocular materials thus avoid unintended angiogenesis; in some aspects, avoiding acidic degradation products achieves this goal. Further, by using hydrogels and hydrophilic materials (components having a solubility in water of at least one gram per liter, e.g., polyethylene glycols/oxides), the influx of inflammatory cells is also minimized; this process is in contrast to conventional use of non-hydrogel or rigid, reservoir-based ocular implants. Moreover, certain proteins may be avoided to enhance biocompatibility; collagen or fibrin glues, for instance, tend to promote inflammation or unwanted cellular reactions since these releases signals as they are degraded that promote biological activity. Instead, synthetic materials are used, or peptidic sequences not normally found in nature. Moreover, the hydrogels may be made without external energy and/or without photoactivation so as to avoid heating or degradation of tissues, bearing in mind that the eye is a sensitive tissue. Additionally, biodegradable materials may be used so as to avoid a chronic foreign body reaction, e.g., as with thermally-formed gels that do not degrade. Further, soft materials or materials made in situ to conform the shape of the surrounding tissues can minimize ocular distortion, and low-swelling materials may be used to eliminate vision-distortion caused by swelling. High pH materials may be avoided, both in the formation, introduction, or degradation phases.

The particles may be prepared with and used to deliver classes of drugs including steroids, non-steroidal anti-inflammatory drugs (NSAIDS), anti-cancer drugs, antibiotics, or others. The particles may be used to deliver drugs and therapeutic agents, e.g., an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). The particles may be used to deliver classes of drugs including steroids, NSAIDS, antibiotics, pain relievers, inhibitors of vascular endothelial growth factor (VEGF), chemotherapeutics, anti viral drugs, for instance. Examples of NSAIDS are Ibuprofen, Meclofenamate sodium, mefanamic acid, salsalate, sulindac, tolmetin sodium, ketoprofen, diflunisal, piroxicam, naproxen, etodolac, flurbiprofen, fenoprofen calcium, Indomethacin, celoxib, ketrolac, and nepafenac. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations.

A variety of drugs or other therapeutic agents may be delivered using these particles or hydrogel-and-particle systems. A list of agents or families of drugs and examples of indications for the agents are provided. The agents may also be used as part of a method of treating the indicated condition or making a composition for treating the indicated condition. For example, AZOPT (a brinzolamide opthalmic suspension) may be used for treatment of elevated intraocular pressure in patients with ocular hypertension or open-angle glaucoma. BETADINE in a Povidone-iodine ophthalmic solution may be used for prepping of the periocular region and irrigation of the ocular surface. BETOPTIC (betaxolol HCl) may be used to lower intraocular pressure, or for chronic open-angle glaucoma and/or ocular hypertension. CILOXAN (Ciprofloxacin HCl opthalmic solution) may be used to treat infections caused by susceptible strains of microorganisms. NATACYN (Natamycin opthalmic suspension) may be used for treatment of fungal blepharitis, conjunctivitis, and keratitis. NEVANAC (Nepanfenac opthalmic suspension) may be used for treatment of pain and inflammation associated with cataract surgery. TRAVATAN (Travoprost ophthalmic solution) may be used for reduction of elevated intraocular pressure—open-angle glaucoma or ocular hypertension. FML FORTE (Fluorometholone ophthalmic suspension) may be used for treatment of corticosteroid-responsive inflammation of the palperbral and bulbar conjunctiva, cornea and anterior segment of the globe. LUMIGAN (Bimatoprost ophthalmic solution) may be used for reduction of elevated intraocular pressure—open-angle glaucoma or ocular hypertension. PRED FORTE (Prednisolone acetate) may be used for treatment of steroid-responsive inflammation of the palpebral and bulbar conjunctiva, cornea and anterior segment of the globe. PROPINE (Dipivefiin hydrochloride) may be used for control of intraocular pressure in chronic open-angle glaucoma. RESTASIS (Cyclosporine ophthalmic emulsion) may be used to increases tear production in patients, e.g., those with ocular inflammation associated with keratoconjunctivitis sicca. ALREX (Loteprednol etabonate ophthalmic suspension) may be used for temporary relief of seasonal allergic conjunctivitis. LOTEMAX (Loteprednol etabonate ophthalmic suspension) may be used for treatment of steroid-responsive inflammation of the palpebral and bulbar conjunctiva, cornea and anterior segment of the globe. MACUGEN (Pegaptanib sodium injection) may be used for Treatment of neovascular (wet) age-related macular degeneration. OPTIVAR (Azelastine hydrochloride) may be used for treatment of itching of the eye associated with allergic conjunctivitis. XALATAN (Latanoprost ophthalmic solution) may be used to reduce elevated intraocular pressure in patients, e.g., with open-angle glaucoma or ocular hypertension. BETIMOL (Timolol opthalmic solution) may be used for treatment of elevated intraocular pressure in patients with ocular hypertension or open-angle glaucoma. Latanoprost is the pro-drug of the free acid form, which is a prostanoid selective FP receptor agonist. Latanoprost reduces intraocular pressure in glaucoma patients with few side effects. Latanoprost has a relatively low solubility in aqueous solutions, but is readily soluble in organic solvents typically employed for fabrication of microspheres using solvent evaporation.

Further embodiments of agents for delivery include those that specifically bind a target peptide in vivo to prevent the interaction of the target peptide with its natural receptor or other ligands. AVASTIN, for instance, is an antibody that binds VEGF. And AFLIBERCEPT is a fusion protein that includes portions of a VEGF receptor to trap VEGF. An IL-1 trap that makes use of the extracellular domains of IL-! (Is this supposed to be IL-1?) receptors is also known; the trap blocks IL-1 from binding and activating receptors on the surface of cells. Embodiments of agents for delivery include nucleic acids, e.g., aptamers. Pegaptanib (MACUGEN), for example, is a pegylated anti-VEGF aptamer. An advantage of the particle-and-hydrogel delivery process is that the aptamers are protected from the in vivo environment until they are released. Further embodiments of agents for delivery include macromolecular drugs, a term that refers to drugs that are significantly larger than classical small molecule drugs, i.e., drugs such as oligonucleotides (aptamers, antisense, RNAi), ribozymes, gene therapy nucleic acids, recombinant peptides, and antibodies.

One embodiment comprises extended release of a medication for allergic conjunctivitis. For instance, ketotifen, an antihistamine and mast cell stabilizer, may be provided in particles and released to the eye as described herein in effective amounts to treat allergic conjunctivitis. Seasonal Allergic Conjunctivitis (SAC) and Perennial Allergic Conjunctivitis (PAC) are allergic conjunctival disorders. Symptoms include itching and pink to reddish eyes. These two eye conditions are mediated by mast cells. Non specific measures to ameliorate symptoms conventionally include: cold compresses, eyewashes with tear substitutes, and avoidance of allergens. Treatment conventionally consists of antihistamine mast cell stabilizers, dual mechanism anti-allergen agents, or topical antihistamines. Corticosteroids might be effective but, because of side effects, are reserved for more severe forms of allergic conjunctivitis such as vernal keratoconjunctivitis (VKC) and atopic keratoconjunctivitis (AKC).

Moxifloxacin is the active ingredient in VIGAMOX, which is a fluoroquinolone approved for use to treat or prevent ophthalmic bacterial infections. Dosage is typically one-drop of a 0.5% solution that is administered 3 times a day for a period of one-week or more.

VKC and AKC are chronic allergic diseases where eosinophils, conjunctival fibroblasts, epithelial cells, mast cells, and/or TH2 lymphocytes aggravate the biochemistry and histology of the conjunctiva. VKC and AKC can be treated by medications used to combat allergic conjunctivitis.

Administration

Embodiments of the invention include administration at or near an eye. The structure of the mammalian eye can be divided into three main layers or tunics: the fibrous tunic, the vascular tunic, and the nervous tunic. The fibrous tunic, also known as the tunica fibrosa oculi, is the outer layer of the eyeball consisting of the cornea and sclera. The sclera is the supporting wall of the eye and gives the eye most of its white color. It is extends from the cornea (the clear front section of the eye) to the optic nerve at the back of the eye. The sclera is a fibrous, elastic and protective tissue, composed of tightly packed collagen fibrils, containing about 70% water.

Overlaying the fibrous tunic is the conjunctiva. The conjunctiva is a membrane that covers the sclera (white part of the eye) and lines the inside of the eyelids. It helps lubricate the eye by producing mucus and tears, although a smaller volume of tears than the lacrimal gland. The conjunctiva is typically divided into three parts: (a) Palpebral or tarsal conjunctivam which is the conjunctiva lining the eyelids; the palpebral conjunctiva is reflected at the superior formix and the inferior formix to become the bulbar conjunctiva, (b) Formix conjunctiva: the conjunctiva where the inner part of the eyelids and the eyeball meet, (c) Bulbar or ocular conjunctiva: the conjunctiva covering the eyeball, over the sclera. This region of the conjunctiva is bound tightly and moves with the eyeball's movements. The conjunctiva effectively surrounds, covers, and adheres to the sclera. It is has cellular and connective tissue, is somewhat elastic, and can be removed, teased away, or otherwise taken down to expose a surface area of the sclera.

The vascular tunic, also known as the tunica vasculosa oculi, is the middle vascularized layer which includes the iris, ciliary body, and choroid. The choroid contains blood vessels that supply the retinal cells with oxygen and remove the waste products of respiration. The nervous tunic, also known as the tunica nervosa oculi, is the inner sensory which includes the retina. The retina contains the photosensitive rod and cone cells and associated neurons. The retina is a relatively smooth (but curved) layer. It does have two points at which it is different; the fovea and optic disc. The fovea is a dip in the retina directly opposite the lens, which is densely packed with cone cells. The fovea is part of the macula. The fovea is largely responsible for color vision in humans, and enables high acuity, which is necessary in reading. The optic disc is a point on the retina where the optic nerve pierces the retina to connect to the nerve cells on its inside.

The mammalian eye can also be divided into two main segments: the anterior segment and the posterior segment. The anterior segment consists of an anterior and posterior chamber. The anterior chamber is located in front of the iris and posterior to the corneal endothelium and includes the pupil, iris, ciliary body and aqueous fluid. The posterior chamber is located posterior to the iris and anterior to the vitreous face where the crystalline lens and zonules fibers are positioned between an anterior and posterior capsule in an aqueous environment.

The cornea and lens help to converge light rays to focus onto the retina. The lens, behind the iris, is a convex, springy disk which focuses light, through the second humour, onto the retina. It is attached to the ciliary body via a ring of suspensory ligaments known as the Zonule of Zinn. The ciliary muscle is relaxed to focus on an object far away, which stretches the fibers connecting it with the lens, thus flattening the lens. Light enters the eye, passes through the cornea, and into the first of two humors, the aqueous humour. Approximately two-thirds of the eye's total refractive power comes from the cornea which has a fixed curvature. The aqueous humor is a clear mass which connects the cornea with the lens of the eye, helps maintain the convex shape of the cornea (necessary to the convergence of light at the lens) and provides the corneal endothelium with nutrients.

The posterior segment is located posterior to the crystalline lens and in front of the retina. It represents approximately two-thirds of the eye that includes the anterior hyaloid membrane and all structures behind it: the vitreous humor, retina, c, and optic nerve. On the other side of the lens is the second humour, the vitreous humour, which is bounded on all sides: by the lens, ciliary body, suspensory ligaments and by the retina. It lets light through without refraction, helps maintain the shape of the eye and suspends the delicate lens.

Figure 2:
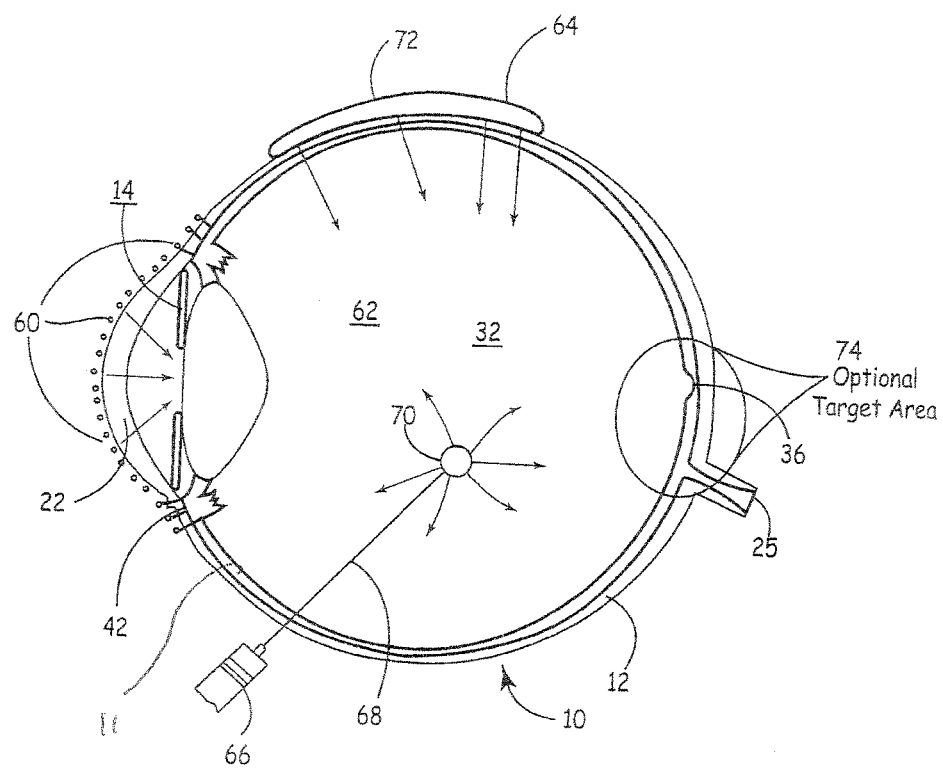
FIG. 2 is a cross-sectional view of an eye, and depicts various points of delivery.

FIG. 2 shows certain points of delivery at or near eye 10. Eye 10 includes sclera 12, iris 14, cornea 22, vitreous body 32, zonular spaces 42, fovea 36, and optic nerve 25. One area for delivery is topically at 60, with area 60 being indicated by dots on surface of eye 10. Another area is intravitreally as indicated by numeral 62, or trans-sclerally, as indicated by numeral 64. In use, for example a syringe 66, catheter (not shown) or other device is used to deliver hydrogel or a hydrogel precursors, optionally through needle 68, into the eye, either intravitrealy, as at 70 or peri-ocularly, as at 72. Another area is subconjunctivally (not shown), below the conjunctiva 12 and above the sclera 11. Drugs or other therapeutic agents are released to the intra-ocular space. In the case of back-of-the-eye diseases, drugs may be targeted via the peri-ocular or intravitreal route to target approximate area 74, where they interact with biological features to achieve a therapy. For instance, hydrogels and/or particles may be delivered to a location adjacent to, or upon, the retina. The hydrogel advantageously is anchored in the vitreous gel and does not allow diffusion of the particles. In contrast, other systems that use a rod or microspheres do not provide anchoring and diffusion or migration in response to movement of, or rubbing of, the eye. The placement of the depot at or near the retina allows a high concentration to be achieved at the retina, with small particles being usable to deliver the drugs for effective treatment. In contrast, spheres, rods, or other shapes that are too large to diffuse or migrate have a volume/surface area ration that is unfavorable for effective controlled release. Another area for placement of a hydrogel and/or particles, or other materials comprising the particles is in a punctum (not shown), e.g., by placing particles in a punctal plug (silicone, polysaccharide, hydrogel, or other material) that is inserted into a punctum of an eye.

Sites where drug delivery depots may be formed in or near an eye include the anterior chamber, the vitreous (intravitreal placement), episcleral, in the posterior subtenon's space (inferior formix), subconjunctival, on the surface of the cornea or the conjunctiva, among others. Periocular drug delivery of an ophthalmic hydrogel implant using subconjunctival, retrobulbar or sub-Tenon's placement has the potential to offer a safer and enhanced drug delivery system to the retina compared to topical and systemic routes.

Figure 3A:
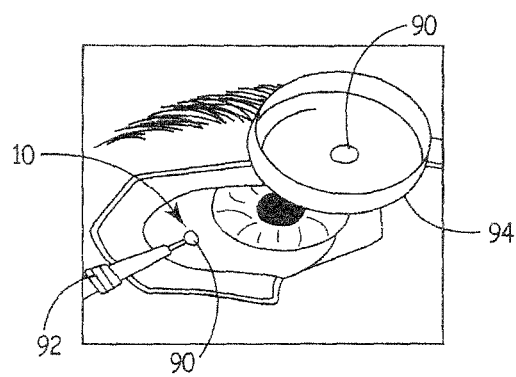
FIG. 3A depicts a magnifying glass in use in a process of injection of a material into an eye.
Figure 3B:
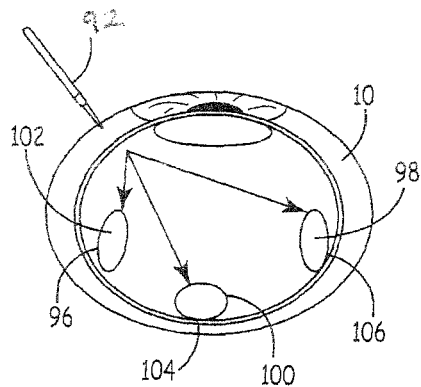
FIG. 3B depicts various placements of the material using the process of FIG. 3A.

An example of in situ placement is illustrated for an intravitreal implant in FIG. 3A. In FIG. 3A, a hydrogel implant is injected intravitrealy about 2.5 mm posterior to the limbus through a pars plana incision 90 using a sub-retinal cannula 92, as shown by depiction of magnifying glass 94 held so as to visualization incision 90 on eye 10, which may be made following dissecting-away or otherwise clearing the conjunctiva, as needed. A sub-retinal cannula 92 (or other appropriate cannulas) is then inserted through incision 90 and positioned intraocularly to the desired target site, e.g., at least one of sites 96, 98, 100 (FIG. 3B) where the flowable precursors are introduced to form a hydrogel in situ. The precursors then forms into an absorbable gel 102, 104, and/or 106, adhering to the desired target site. Particles comprising a therapeutic agent may be included in the gel or gels. Significantly, it is possible to use a fine gauge needle to plate the precursors. Embodiments include placement with a 25 gauge needle. Further embodiments include using a needle smaller in diameter than 25 gauge, e.g., 26, 27, 30, 31, 32 gauge.

FIntravitreal in situ implant embodiments can improve the efficacy and pharmacokinetics of potent therapeutic agents in the treatment of eye diseases and minimize patient side effects in several ways. First, the implant can be placed in the vitreous cavity at a specific disease site, bypassing the topical or systemic routes and thereby increasing drug bioavailability. Secondly, the implant maintains local therapeutic concentrations at the specific target tissue site over an extended period of time. Thirdly, the number of intravitreal injections would be substantially reduced over a 12 month therapy regimen, thereby reducing patient risk of infection, retinal detachment and transient visual acuity disturbances (white specks floating in the vitreous) that can occur until the drug in the vitreous migrates down toward the inferior wall of the eye and away from the portion of the central vitreous or macula.

The hydrogels may be formed on scleral tissue either with or without the presence of the conjunctiva. The hydrogel may be adhesive to the sclera or other tissue near the sclera to promote drug diffusion through the intended tissue or to provide a stable depot to direct the therapeutic agents as required. In some embodiments, the conjunctiva of the eye may be removed, macerated, dissected away, or teased-free so that the tissue can be lifted away from the sclera to access a specific region of the sclera for implantation or injection of the hydrogel. A hydrogel is formed in situ that makes a layer on, and adheres, to the surface area. The conjunctiva may be allowed to contact the tissue if it is still present or retains adequate mechanical integrity to do so. In some embodiments the hydrogel is comprised of at least 50%, 75%, 80%, 90%, or 99% w/w water-soluble precursors (calculated by measuring the weight of the hydrophilic precursors and dividing by the weight of all precursors, so that the weight of water or solvents or non-hydrogel components is ignored) to enhance the non-adhesive properties of the hydrogel. In some embodiments, such hydrophilic precursors substantially comprise PEOs. In some embodiments, drugs to reduce tissue adherence mediated by biological mechanisms including cell mitosis, cell migration, or macrophage migration or activation, are included, e.g., anti-inflammatories, anti-mitotics, antibiotics, PACLITAXEL, MITOMYCIN, or taxols.

In other embodiments, the sclera is not substantially cleared of the conjunctiva. The conjunctiva is a significant tissue mass that overlays much or all of the sclera. The conjunctiva may be punctured or penetrated with a needle or catheter or trocar and precursors introduced into a space between the sclera and conjunctiva. This placement of the implant is referred to as a subconjunctival location. In some cases the conjunctiva may be punctured to access a natural potential space between the tissues that is filled by the precursors. In other cases, a potential or actual space is created mechanically with a trocar, spreader, or the like, that breaks the adherence between the sclera and conjunctiva so that precursors may be introduced. The conjunctiva has enough elasticity to allow useful amounts of precursors to be introduced or forced into such natural or created spaces. Accordingly, in some cases, the amount is between about 0.25 to about 5 ml; artisans will immediately appreciate that all the ranges and values within the explicitly stated ranges are contemplated, e.g., about 1 ml or from 0.5 ml to about 1.5 ml.

Moreover, removal of a hydrogel, whether present intraocularly or periocularly, is also readily achieved using either a vitrectomy cutter if the implant is located in the vitreous cavity or a manual I/A syringe and cannula if the implant is located on the scleral surface or irrigation/aspiration handpiece. This contrasts with major surgical procedures needed for the removal of some conventional non-absorbable implants.

In further embodiments, a material may be placed into the patient, e.g., in a tissue or organ, including subcutaneous, intramuscular, in a potential space of a body, or in a natural cavity or opening. The material provides a depot for release of an agent over time.

The materials described herein may be used to deliver drugs or other therapeutic agents (e.g., imaging agents or markers). One mode of application is to apply a mixture of precursors and other materials (e.g., therapeutic agent, buffer, accelerator, initiator) through a needle, cannula, catheter, or hollow wire to a site. The mixture may be delivered, for instance, using a manually controlled syringe or mechanically controlled syringe, e.g., a syringe pump. Alternatively, a dual syringe or multiple-barreled syringe or multi-lumen system may be used to mix the precursors at or near the site.

The hydrogels may be provided in flowable form to the site, e.g., as flowable precursors. The precursors may be dissolved in, or suspended in, a liquid and applied to the site. The precursors combine in situ to form a hydrogel having a unitary continuous phase.

In some aspects, in-situ formation of the hydrogel lets the hydrogel gel or crosslink in place, so that it does not flow back out through the tract of the needle and diffuse through the incision site upon the removal of the needle or cannula. A shape-stable hydrogel thus formed can effectively deliver the drug and advantageously can have well-controlled size, shape, and surface area. A small needle may be used to inject the materials since soluble or flowable precursors may be used instead of an already-formed material. By way of contrast, alternative materials that do not cross-link quickly and firmly upon introduction tend to flow back out of the incision. And materials that do not covalently cross-link are subject to creep or weeping as the material continually reorganizes and some or all of the material flows out.

An alternative to in situ formation of the covalent cross-links in the gel is to pre-form the gel ex vivo and then introduce the material into the body. For example, the hydrogels may be provided in vivo as a plurality of hydrogel particles that substantially contact each other. The hydrogel particles may be made to have a lubricity and maximum diameter for manual passage out of a syringe through a 3 to 5 French catheter, or a 10 to 30 gauge needle. Artisans will immediately appreciate that all the ranges and values within the explicitly stated ranges are contemplated, e.g., 25 to 30 gauge. The use of small needles is particular advantageous in the eye, which is a sensitive organ. Applications to other organs are also advantageous, e.g., to control bleeding or other damage. The particles may be formed by creating a hydrogel and then breaking it up into smaller pieces. The material may be, e.g., ground in a ball mill or with a mortar and pestle, or chopped or diced with knives or wires. Or the material may be cut-up in a blender. Another process involves forcing the material through a mesh, collecting the fragments, and passing them through the same mesh or another mesh until a desired size is reached. The hydrogel may contain the therapeutic agent-loaded particles. Some or all of the hydrogel particles may contain the therapeutic agent-loaded particles. In some embodiments, a first set of therapeutic agent-loaded particles loaded with a first therapeutic agent is included inside a first set of hydrogel particles and a second set of therapeutic agent-loaded particles loaded with a second therapeutic agent is included inside a second set of hydrogel particles. In this manner, a plurality of agents may be released from a single implant. Embodiments of the particles include those with a particular shape such as sphere, rod, or disc.

Embodiments include placement of a plurality of hydrogel particles. The hydrogel particles may comprise lipophilic particles that comprise a therapeutic agent, e.g., a protein such as an anti-VEGF. The particles may be made with a sized for manual passage through a 30-gauge or smaller diameter needle. The pressure to force the particles through the needle may be provided manually.

Kits

Kits or systems for making hydrogel-lipophilic particle systems may be prepared. Applicators may be used in combination with the particles and/or hydrogel. The kits are manufactured using medically acceptable conditions and contain components that have sterility, purity and preparation that is pharmaceutically acceptable. The kit may contain an applicator as appropriate, as well as instructions. Low water soluble lipophilic particles comprising a therapeutic agent may be included pre-mixed or available for mixing. The hydrogel components may be provided as: one or more precursors that form the hydrogel in situ, as a plurality of particles that are placed into the patient, or as a unitary implant. The lipophilic particles may be in one or more of the precursors, in the unity implant, or in at least a portion of the particles. Solvents/solutions may be provided in the kit or separately, or the components may be pre-mixed with the solvent. The kit may include syringes and/or needles for mixing and/or delivery. The kit or system may comprise components set forth herein.

One system uses a dual container applicator, e.g, double barreled syringe, for delivering at least one precursor. One syringe may have least one precursor and the other syringe may have an activator for activating the precursor, e.g., an initiator. Or each syringe may have a precursor, with the precursors making a matrix as a result of mixing. Lipophilic particles comprising a therapeutic agent are provided in the kit for mixing (or pre-mixed with) at least one of the precursors.

The hydrogel in a kit may be dehydrated or desiccated. One embodiment provides hydrogels that are 30% to 100% desiccated; artisans will immediately appreciate that all the ranges and values within the explicitly stated ranges are contemplated. In the case of a unitary implant, the hydrogel may be passed through a needle or an opening into an eye or an area at or near the eye. After placement, the hydrogel may swell. The swelling may be low-swelling as already described, or may be large, e.g., 100 to 1000%; artisans will immediately appreciate that all the ranges and values within the explicitly stated ranges are contemplated, e.g., between 100 and 300%.

Other embodiments provide a single applicator, e.g., one syringe, that comprises hydrogel particles for delivery. One embodiment provides a container for hydrogel particle delivery (e.g., syringe barrel, vial with septum) that does not require the addition of further contents, e.g., the hydrogel particles are used neat, or are already in a solution or slurry that will be placed into the patient. This allows for the use of injectable preformed hydrogel slurries, eliminating the need for reconstitution, multiple syringes, and allowing for stop-and-start injections without fear of needle plugging. The hydrogel particle solvent may be essentially water, meaning about 99% v/v of the solvent is water, with salts or buffers being present as desired. Other solvents may be used that are safe and biocompatible, e.g., dimethylsulfoxide. The hydrogel particles may further comprise therapeutic agent-loaded lipophilic particles.

EXAMPLES

Example 1A: Laurie Acid/Protein Particles

Ovalbumin was ground to a fine powder using a mortar and pestle. 200 mg of the ground ovalbumin was added to 800 mg of lauric acid and heated to 48° C. in a 20 mL scintillation vial while stirring with a magnetic stir bar to uniformly suspend the ovalbumin particles. The vial was then cooled to solidify the lauric acid phase. The solidified mixture was then ground to a powder using a mortar and pestle.

Example 1B: Laurie Acid/Protein Particles

Ovalbumin was ground to a fine powder using a mortar and pestle and sieved to <20µ diameter. 200 mg of the ground ovalbumin was added to 800 mg of lauric acid and heated to 48° C. in a 20 mL scintillation vial while stirring with a magnetic stir bar to uniformly suspend the ovalbumin particles. The suspension was transferred to a plastic syringe and cooled to solidify the lauric acid phase into a pellet (approximately 1 g). A solution (200 mL) of 6% by weight of USP polyvinylalcohol (PVA) was heated to 54° C. in a 400 mL beaker with vigorous stirring using an impeller rotating at 700 rpm and the ovalbumin-lauric acid (O-LA) pellet was dropped into the stirred PVA solution. The pellet melted and dispersed to form an emulsion. Stirring was continued for 30 seconds and then the emulsion was poured into an excess of iced deionized water to solidify the O-LA particles. The solid particles were isolated by filtration and dried under vacuum overnight.

Example 2: Methyl Stearate Particles

Ovalbumin was ground to a fine powder using a mortar and pestle. 200 mg of the ground ovalbumin was added to 800 mg of methyl stearate and heated to 40° C. in a 20 mL scintillation vial while stirring with a magnetic stir bar to uniformly suspend the ovalbumin particles. The vial was then cooled to solidify the methyl stearate phase. The solidified mixture was then ground to a powder using a mortar and pestle.

Example 3: Methyl Palmitate Protective Coating Preparation

Ovalbumin was ground to a fine powder using a mortar and pestle. 200 mg of the ground ovalbumin was added to 800 mg of methyl palmitate and heated to 46° C. in a 20 mL scintillation vial while stirring with a magnetic stir bar to uniformly suspend the ovalbumin particles. The vial was then cooled to solidify the methyl palmitate phase. The solidified mixture was then ground to a powder using a mortar and pestle.

Example 4: Gel Sample Preparation

The powder from Examples 1, 2 or 3 were combined with a polyethylene glycol (PEG) precursor to form hydrogel samples for testing. One PEG used was 8 arm 15000 Dalton PEG terminated on each arm with succinimidylsuccinate (SS) end groups (8a15K PEG SS). A second PEG used was 8 arm 15000 Dalton PEG terminated on each arm with succinimidylglutarate (SG) end groups (8a15K PEG SG). Gel formation was accomplished by first combining 31 mg of powder from examples 1, 2 or 3 with 57 mg of 8a15K PEG SS or 8a15K PEG SG. The PEG/powder mixture was then combined with 200 uL of Diluent (17.4 mg/mL trilysine acetate and 1.2 mg/mL sodium phosphate monobasic) to form a precursor suspension. The precursor suspension was then combined with an Accelerator solution (27.6 mg/mL sodium phosphate dibasic and 8.7 mg/mL sodium tetraborate decahydrate) to form a gel cylinder containing suspended coated ovalbumin particles.

Example 5: Measurement of Ovalbumin Recovery

A sample of ovalbumin-methyl palmitate powder (O-MP) was prepared as in Example 3. A portion of this powder was encapsulated in 8a15K PEG SS as in example 4 (O-MP-SS). Ovalbumin-methyl stearate powder (O-MS) was prepared according to example 2. A portion of this powder was encapsulated in 8a15K PEG SS as in example 4 (O-MS-SS). These samples were placed in a PBS solution for 1 and 3 days and tested for recovery of the albumin by HPLC analysis.

TABLE 2

| | % Protein Recovered | |
|---|---|---|
| Sample | 1 Day at 37° C. in PBS | 3 Days at 37° C. in PBS |
| O-MP | 103 | 107 |
| O-MP-SS | 19 | 38 |
| O-MS | 106 | 108 |
| O-MS-SS | 28 | 47 |

The results show the complete recovery at day 1 of the albumin coated with methyl palmitate and methyl stearate, but the gel coated samples showed a gradual release indicating the gel is required to control the release rate of the protein.

Example 6: Release of Protein from Particles of Lauric Acid Disposed with a Gel Matrix Ovalbumin was coated with Laurie acid as in example 1 (O-LA). The powder was then coated with 8a15K PEG SS/trilysine as in example 4 (O-LA-SS). The O-LA-SS was placed in PBS and tested for protein released into the PBS at 1, 3, 5 and 7 days with complete change of buffer at each time point. The buffer at each time point was tested by HPLC for the presence of ovalbumin. The results are shown in the table below.

| Days at 37° C. in PBS | % Protein recovered by HPLC |
|---|---|
| 1 | 12 |
| 3 | 22 |
| 5 | 67 |
| 7 | 92 |

These data show the controlled release of the protein with nearly full recovery after one week.

Example 7: Lauric Acid Protective Coating Preparation with Excluded Oxygen

An ATMOSBAG glove bag was filled with cryogenic nitrogen to exclude oxygen which may affect protein stability. All subsequent sample preparation steps were then conducted under Nitrogen in the glove bag. Ovalbumin was ground to a fine powder using a mortar and pestle. 200 mg of the ground ovalbumin was added to 800 mg of lauric acid and heated to 48° C. in a 20 mL scintillation vial while stirring with a magnetic stir bar to uniformly suspend the ovalbumin particles. The vial was then cooled to solidify the lauric acid phase. The solidified mixture was then ground to a powder using a mortar and pestle.

Example 8: Controlled Release and Recovery

A sample of albumin (ovalbumin) in lauric acid particles (O-LA) disposed inside a hydrogel comprised of the reaction product of precursors of 8a15K PEG SG and trilysine (O-LA-SG, referring the O-LA in the hydrogel) was prepared as in Example 5 and Example 4. This sample was placed in physiologically buffered phosphate buffered saline (PBS) at 37° C. The release of the protein was quantified by high pressure liquid chromatography (HPLC), with the data shown in Table 3.

TABLE 3

| Quantification of amount of released protein | |
|---|---|
| Days | % Protein Recovered |
| 0 | 0 |
| 1 | 21.4 |
| 3 | 25.7 |
| 5 | 26.8 |
| 7 | 27.4 |
| 9 | 27.9 |
| 11 | 28.5 |
| 12 | 29.3 |
| 15 | 30.2 |
| 21 | 32.5 |
| 23 | 33.7 |
| 27 | 37.1 |
| 29 | 40.8 |
| 33 | 50.1 |
| 35 | 65.1 |

TABLE 3-continued

Quantification of amount of released protein

| Days | % Protein Recovered |
|---|---|
| 37 | 69.6 |
| 40 | 82.7 |
| 42 | 86.8 |
| 44 | 90.0 |
| 49 | 90.3 |
| 51 | 90.3 |
| 56 | 90.3 |

Figure 4:
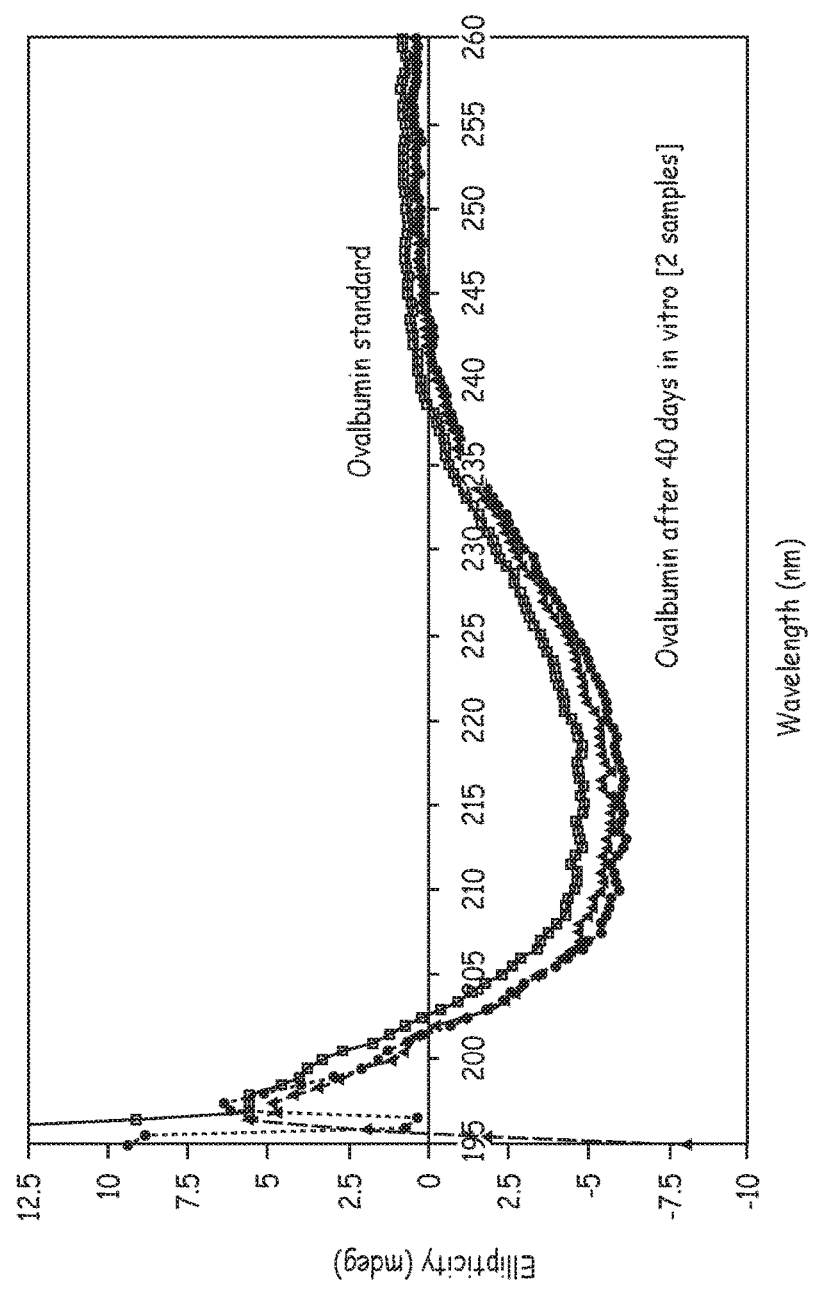
FIG. 4 is the result of a circular dichroism test of proteins released from lipophilic particles as compared to various controls.

These data show the controlled release of the ovalbumin over 56 days with nearly full recovery of the protein. At day 40 a sample of the PBS solution was tested be circular dichroism CD analysis to monitor for any changes in protein structure. The results are shown in FIG. 4. The results show no wavelength shift, indicating no significant change in structure.

Example 9: Injectable Form Preparation

A sample of O-LA was prepared as in Example 5. A portion of the O-LA powder was entrapped within 8a15K PEG SS/trilysine to prepare a sample of O-LA-SS as in Example 4. This material was broken up by forcing it through a 150 µm sieve three times. A portion of the crushed gel was placed in a 1 mL syringe and was shown to pass through a 30 gauge needle. Two samples of each material were placed in PBS at 37° C. to monitor recovery of the protein over time. The results are shown in Table 4. The data shows that the crushed gel was still able to control the release of the protein to a similar extent as the gel in cylinder form.

TABLE 4

Recovery and release of agent from particles

| | % Protein Recovered | | | | | |
|---|---|---|---|---|---|---|
| | O-LA | | O-LA-SS | | Crushed O-LA-SS | |
| Days at 37° C. in PBS | Sample 1 | Sample 2 | Sample 1 | Sample 2 | Sample 1 | Sample 2 |
| 1 | 72% | 74% | 13% | 13% | 13% | 12% |
| 2 | — | — | 10% | 15% | 19% | 16% |
| 3 | — | — | 22% | 27% | 35% | 25% |
| 5 | — | — | 85% | 105% | 94% | 72% |
| 7 | — | — | 86% | 104% | 90% | 83% |

Example 10: Stability of Ovalbumin During Processing

Samples of O-LA were prepared as in Example 5. Samples at each step of the process were collected and analyzed by Isoelectric focusing (IEF) which measures the isoelectric point (pI) of the protein. A shift in pI of more than 0.2 is indicative of a single deamidation reaction. All samples had pI values that indicated no deamidation had occurred. The same samples were analyzed by ELISA. The ELISA tests indicated no denaturation of the epitope had occurred. These results demonstrate ovalbumin can undergo these process steps with no loss of stability and were not denatured.

TABLE 5

Stability of released proteins

| | | IEF data | | | | Protein Recovery |
|---|---|---|---|---|---|---|
| | | Ovalbumin $A_1$ | | Ovalbumin $A_2 + A_3$ | | (%) by ELISA |
| Description | Sample | % | pI | % | pI | % |
| Albumin powder | 1 | 80.9 | 5.10 | 19.1 | 5.14 | 110 |
|  | 2 | 82.2 | 5.09 | 17.8 | 5.14 | 82 |
| Ground Albumin powder | 1 | 81.7 | 5.10 | 18.3 | 5.15 | 100 |
|  | 2 | 81.2 | 5.11 | 18.8 | 5.15 | 105 |
| Coated Albumin microparticles | 1 | 80.3 | 5.05 | 19.7 | 5.11 | 114 |
|  | 2 | 80.9 | 5.08 | 19.1 | 5.13 | 84 |

Example 11: Hydrogel Degradation Tuning

A composition of precursors was adjusted by choosing various functional groups to thereby adjust a range of degradation times. Four-armed polyethylene glycol precursors (4a20K) with a electrophilic reactive functional groups were mixed with a trilysine precursor in the presence of microparticles.

Gel plugs were manufactured using four different functional groups: 4a20KSG (Glutarate), 4a20KSAP (Adipate), 4a20KSAZ (Azelate) and 4a20KSGA (Glutaramide). The final microspheres load per total volume of plug was kept constant (20%). The final polymer per total liquid was kept constant (9%). The pH of the Trilysine acetate/Sodium Phosphate dibasic was adjusted when necessary using Sodium hydroxide (NaOH) to achieve a gel time between 2 and 3 minutes. The trilysine acetate ratio to polymer was adjusted accordingly for each lot of polymer based on its functional group substitution %.

Three tubes A, B, C (3 ml syringes) were prepared to formulate before injection and casting in silicone tubes for plug formation: Tube A: Polymer powder and WFI; Tube B: Placebo 4A100PLA microspheres and WFI; Tube C: Trilysine acetate, Sodium phosphate dibasic solution (40 mM) with pH adjusted as needed to achieve 2-3 minutes gel time.

Components of Tube A and B were mixed first then mixed with components of Tube C. Recorded gel times were as follows:

4a20KSG 2'19" (no pH adjustment)
4a20KSAP 2'54" (no pH adjustment)
4a20KSAZ 2'28" (pH of Tube C adjusted to 8.35)
4a20KSGA 2'33" (no pH adjustment)

The final mixture was then quickly injected vertically for casting in silicone tubing (Tubing ID: 1.58 mm ($\frac{1}{16}^{th}$ ID×$\frac{3}{16}^{th}$ OD, 25 cm)). After rolling for 3 minutes all samples were left to cure for 1 h 40 minutes. Samples were Immediately cut, weighed, measured and placed in PBS at 55° C. Samples were weighed occasionally until swelling reached 300-350%. Samples were monitored by visual inspection daily until gel component disappeared
Results:

| Sample | Days at 55° C. to 300-350% swelling | Days at 55° C. to full disappearance |
|---|---|---|
| 4a20K SG | 5 | 7 |
| 4a20K SAP | 7 | 9 |
| 4a20K SAZ | 12 | 13 |

It is claimed:

1. A medical material comprising
a biodegradable hydrophilic hydrogel comprising dispersed lipophilic microparticles that have a diameter from 1-500 microns and consist essentially of a low water soluble lipophilic compound that has a solubility in 20° C. distilled water that is from 0.001 to 0.5 mg/ml and a therapeutic protein having a secondary and/or a tertiary structure disposed as a solid particle of less than 20 microns diameter in the microparticles, with the microparticles having no more than 4 parts of the lipophilic compound for every one part of the therapeutic protein on a w/w basis, with the particle releasing 100% the protein in less than 24 hours in the absence of the hydrogel upon exposure to physiological solution.

2. The medical material of claim 1 wherein the low water soluble lipophilic compound has a molecular mass of no more than about 2000 Daltons.

3. The medical material of claim 1 wherein the microparticles have a melting point of between about 25° C. and about 60° C.

4. The medical material of claim 1 wherein the low water soluble lipophilic compound has a logP of at least about 2.

5. The medical material of claim 3 wherein the lipophilic microparticles are a solid at physiological temperature.

6. The medical material of claim 1 wherein the hydrogel comprises covalently crosslinked hydrophilic polymers.

7. The medical material of claim 6 wherein the polymers comprise a member chosen from the group consisting of polyethylene oxide, polyvinyl pyrrolidinone, hyaluronic acid, and polyhydroxyethlymethacrylate.

8. The medical material of claim 1 wherein the hydrogel biodegrades by spontaneous hydrolysis of hydrolytically degradable linkages chosen from the group consisting of esters, carbonates, anhydrides and orthocarbonates.

9. The medical material of claim 1 wherein the hydrogel comprises ionically crosslinked polymers.

10. The medical material of claim 9 wherein the polymers comprise a member chosen from the group consisting of alginate, gellan, collagen, and polysaccharide.

11. The medical material of claim 1 wherein a cumulative amount of release of the agent reaches 90% of the agent at a time between about 1 month and about 6 months after placement of the hydrogel and particles in a physiological solution.

12. The medical material of claim 1 wherein the lipophilic microparticles comprise at least one member chosen from the group consisting of lauric acid, methyl stearate, and methyl palmitate.

13. A process of making a medical material comprising
coating a protein powder with a low water soluble lipophilic compound that, has a solubility in 20° C. distilled water that is from 0.001 to 0.5 mg/ml to make microparticles that have a diameter from 1-500 microns and that consist essentially of the protein disposed as a solid particle of less than 20 microns diameter in the microparticles and the low water soluble lipophilic compound, with the microparticles having no more than 4 parts of the lipophilic compound for every one part of the therapeutic protein on a w/w basis, with the particle releasing 100% the protein in less than 24 hours upon exposure to physiological solution and
dispersing the particles in a medical hydrogel implant, and
with the protein having a secondary and/or a tertiary structure.

14. The process of claim 13 wherein the lipophilic compound comprises a fatty acid with a melting point between about 25° C. and about 60° C.

15. The process of claim 13 wherein the low water soluble lipophilic compound has a molecular mass of no more than about 2000 Daltons.

16. The process of claim 13 wherein the lipophilic compound is provided as a melt, and wherein coating a protein powder with a lipophilic compound to make microparticles comprises mixing the powder with the melt to coat the powder with the compound, cooling the mixture to a solid, and breaking up the solid to form the microparticles.

17. The process of claim 13 wherein the hydrogel is formed in a shape chosen from the group consisting of a rod and a disc.

18. The process of claim 13 further comprising dehydrating the hydrogel for storage.

19. The process of claim 13 wherein the hydrogel is formed in situ in a patient.

20. The process of claim 19 wherein the microparticles are mixed r with a precursor that is reacted to form the hydrogel in situ.

21. The process of claim 20 wherein the precursor is reacted by a technique chosen from the group consisting of free radical polymerization and thermally sensitive gelation in response to a body temperature of the patient.

22. The process of claim 20 wherein the precursor is a first precursor comprising nucleophilic groups, and further comprising reacting the first precursor with the second precursor comprising electrophilic groups, with the electrophilic groups and nucleophilic groups reacting with each other to form covalent bonds to thereby form the hydrogel.

23. The process of claim 13 wherein coating, a protein powder with the lipophilic compound to make microparticles comprises mixing the protein powder with the lipophilic compound to form a mixture of the powder and the compound, dispersing the mixture into a solution to form droplets of the mixture, and cooling the droplets to a solid phase and thereby forming the microparticles.

24. The process of claim 23 wherein cooling the droplets comprises providing the solution as a non-solvent for the lipophilic compound at a temperature below the melting point of the lipophilic compound.

25. The process of claim 13 further comprising providing the hydrogel as a plurality of hydrogel microparticles.

26. The process of claim 13 wherein the particles are dehydrated for storage and, at the time of use, mixed with a carrier to form a slurry that is injectable into a patient.

27. The process of claim 13 wherein the microparticles have a melting point between about 25° C. and about 60° C.

28. The process of claim 13 wherein the micro articles are solid at physiological temperatures in vivo and have a melting point of less than about 60° C.

29. The process of claim 13 wherein the peptide in the particle is substantially free of denaturation as measurable by comparison of the protein in the microparticle to the protein before mixing with the hydrophobic coating, with the comparison being made by enzyme-linked immunosorbent assay and isoelectric focusing.

30. The process of claim 13 wherein, after placement of the medical material in an excess of physiological solution at, physiological temperature, a cumulative amount of release of the agent reaches 90% of the agent at a time between about 1 and about 6 months after placement of the hydrogel and particles in a saline solution.

31. A method of delivering a therapeutic agent to a patient comprising placing the medical material of claim 1 in a patient, with the therapeutic agent being released into the patient.

32. The method of claim 31 wherein the hydrogel is molded into a unitary implant that is subsequently implanted in the patient.

33. The method of claim 31 wherein the implant is implanted in a substantially dehydrated state.

34. The method of claim 31 wherein the hydrogel is an injectable suspension or slurry that is injected into the patient.

35. The method of claim 31 wherein the hydrogel is placed into the patient at or near an eye at a location chosen from the group consisting of intravitreal, cornea, retinal, subconjunctival, scleral, and punctal.

36. The method of claim 31 wherein the hydrogel is placed through a 25 gauge or finer needle into the target tissue.

37. The method of claim 31 wherein the hydrogel is placed in a tissue, in an organ, subcutaneously, or intramuscularly.

38. The medical material of claim 1 wherein the lipophilic microparticles are solid at 20° C., with the protein being released from the microparticles and the medical material in a conformation that is substantially free of denaturation as measurable by enzyme-linked immunosorbent assay, and isoelectric focusing.

39. The method of claim 13 with the protein being released from the microparticles and the medical material in a conformation that is substantially free of denaturation as measurable by enzyme-linked immunosorbent assay and isoelectric focusing.

40. The method of claim 31 with the protein being released from the microparticles and the medical material in a conformation that is substantially free of denaturation as measurable by enzyme-linked immunosorbent assay and isoelectric focusing.

* * * * *

UNITED STATES PATENT AND TRADEMARK OFFICE
CERTIFICATE OF CORRECTION

| | |
|---|---|
| PATENT NO. | : 10,226,417 B2 |
| APPLICATION NO. | : 13/234428 |
| DATED | : March 12, 2019 |
| INVENTOR(S) | : Jarrett et al. |

Page 1 of 1

It is certified that error appears in the above-identified patent and that said Letters Patent is hereby corrected as shown below:

In the Claims

In Column 36, Claim 20, Line 21, delete "mixed r" and insert -- mixed --, therefor.

In Column 36, Claim 28, Line 53, delete "micro articles" and insert -- microparticles --, therefor.

In Column 36, Claim 30, Line 64, delete "at," and insert -- at --, therefor.

Signed and Sealed this
Sixteenth Day of July, 2019

Andrei Iancu
*Director of the United States Patent and Trademark Office*